(12) United States Patent
McInturf et al.

(10) Patent No.: US 12,029,942 B2
(45) Date of Patent: Jul. 9, 2024

(54) SYSTEM AND METHOD FOR REMOTELY PROVIDING AND MONITORING PHYSICAL THERAPY

(71) Applicant: Band Connect Inc., Cincinnati, OH (US)

(72) Inventors: Abigail McInturf, Cincinnati, OH (US); Rohit Nayak, Cincinnati, OH (US)

(73) Assignee: Band Connect Inc., Cincinnati, OH (US)

( * ) Notice: Subject to any disclaimer, the term of this patent is extended or adjusted under 35 U.S.C. 154(b) by 0 days.

(21) Appl. No.: 18/042,358

(22) PCT Filed: Aug. 26, 2021

(86) PCT No.: PCT/US2021/047713
§ 371 (c)(1),
(2) Date: Feb. 21, 2023

(87) PCT Pub. No.: WO2022/047006
PCT Pub. Date: Mar. 3, 2022

(65) Prior Publication Data
US 2023/0347210 A1    Nov. 2, 2023

Related U.S. Application Data

(60) Provisional application No. 63/071,762, filed on Aug. 28, 2020.

(51) Int. Cl.
*A63B 24/00*     (2006.01)
*A63B 71/06*     (2006.01)
(Continued)

(52) U.S. Cl.
CPC ...... *A63B 24/0006* (2013.01); *A63B 24/0062* (2013.01); *A63B 24/0075* (2013.01);
(Continued)

(58) Field of Classification Search
CPC ............ A63B 24/0006; A63B 24/0062; A63B 24/0075; A63B 71/0619; A63B 2225/20;
(Continued)

(56) References Cited

U.S. PATENT DOCUMENTS

| 9,273,967 B2 | 3/2016 | Ding et al. |
| 2011/0054870 A1* | 3/2011 | Dariush ................. G16H 50/50 348/46 |

(Continued)

OTHER PUBLICATIONS

The International Bureau of WIPO, International Preliminary Report On Patentability, International Application No. PCT/US2021/047713, dated Feb. 28, 2023 (7 pages).

(Continued)

*Primary Examiner* — Mark Edwards
(74) *Attorney, Agent, or Firm* — Wood Herron & Evans LLP

(57) ABSTRACT

An apparatus, a method, and a computer program product for use in performing, monitoring, and evaluating the performance of therapeutic exercises. The apparatus includes a human-device interface and a motion sensor. In response to movement of the human-device interface, a controller receives motion data from the motion sensor, and transmits the motion data to a computing device. Based on the motion data, the computing device displays a graphical element that depicts the movement. The computing device compares the movement to a target motion, and if the movement matches the target motion, displays a graphical element indicating an exercise is being performed properly. If the movement does not match the target motion, the computing device indicates the exercise is not being performed properly and displays another graphical element indicating how to correct the motion.

21 Claims, 32 Drawing Sheets

(51) Int. Cl.
*G06F 3/01* (2006.01)
*G06F 3/16* (2006.01)
*G06T 13/80* (2011.01)
*G16H 20/30* (2018.01)
*G16H 40/67* (2018.01)

(52) U.S. Cl.
CPC .......... *A63B 71/0619* (2013.01); *G06F 3/011* (2013.01); *G06F 3/016* (2013.01); *G06F 3/167* (2013.01); *G06T 13/80* (2013.01); *G16H 20/30* (2018.01); *G16H 40/67* (2018.01); *A63B 2024/0009* (2013.01); *A63B 2024/0068* (2013.01); *A63B 2071/0647* (2013.01); *A63B 2071/0655* (2013.01); *A63B 2214/00* (2020.08); *A63B 2220/51* (2013.01); *A63B 2220/56* (2013.01); *A63B 2220/803* (2013.01); *A63B 2225/20* (2013.01); *G06T 2200/24* (2013.01)

(58) Field of Classification Search
CPC ........ A63B 2214/00; A63B 2024/0009; A63B 2024/0068; A63B 2071/0647; A63B 2071/0655; A63B 2220/51; A63B 2220/56; A63B 2220/803; G16H 20/30; G16H 20/67; G06F 3/011; G06F 3/016; G06F 3/167; G06T 2200/24; G06T 13/80
USPC .......................................................... 345/156
See application file for complete search history.

(56) References Cited

U.S. PATENT DOCUMENTS

| | | | |
|---|---|---|---|
| 2013/0123667 A1 | 5/2013 | Komatireddy et al. | |
| 2013/0196825 A1* | 8/2013 | Silagy .................. | A63B 21/023 482/49 |
| 2014/0074179 A1* | 3/2014 | Heldman ............. | A61B 5/1101 607/45 |
| 2014/0194251 A1* | 7/2014 | Reich ............... | A63B 21/00178 482/6 |
| 2018/0056128 A1 | 3/2018 | Narasimha Rao et al. | |
| 2018/0121728 A1* | 5/2018 | Wells .................... | A61B 5/1116 |
| 2020/0289890 A1* | 9/2020 | Kim ....................... | G01C 19/00 |

OTHER PUBLICATIONS

Manon Kok et al . . . , (2017), "Using Inertial Sensors for Position and Orientation Estimation", Foundations and Trends In Signal Processing: vol. 11: No. 1-2, pp. 1-153, http://dx.doi.org/10.1561/2000000094 (90 pages).

International Searching Authority / US, International Search Report and the Written Opinion of the International Searching Authority, International Application No. PCT/US2021/047713, dated Nov. 17, 2021 (11 pages).

* cited by examiner

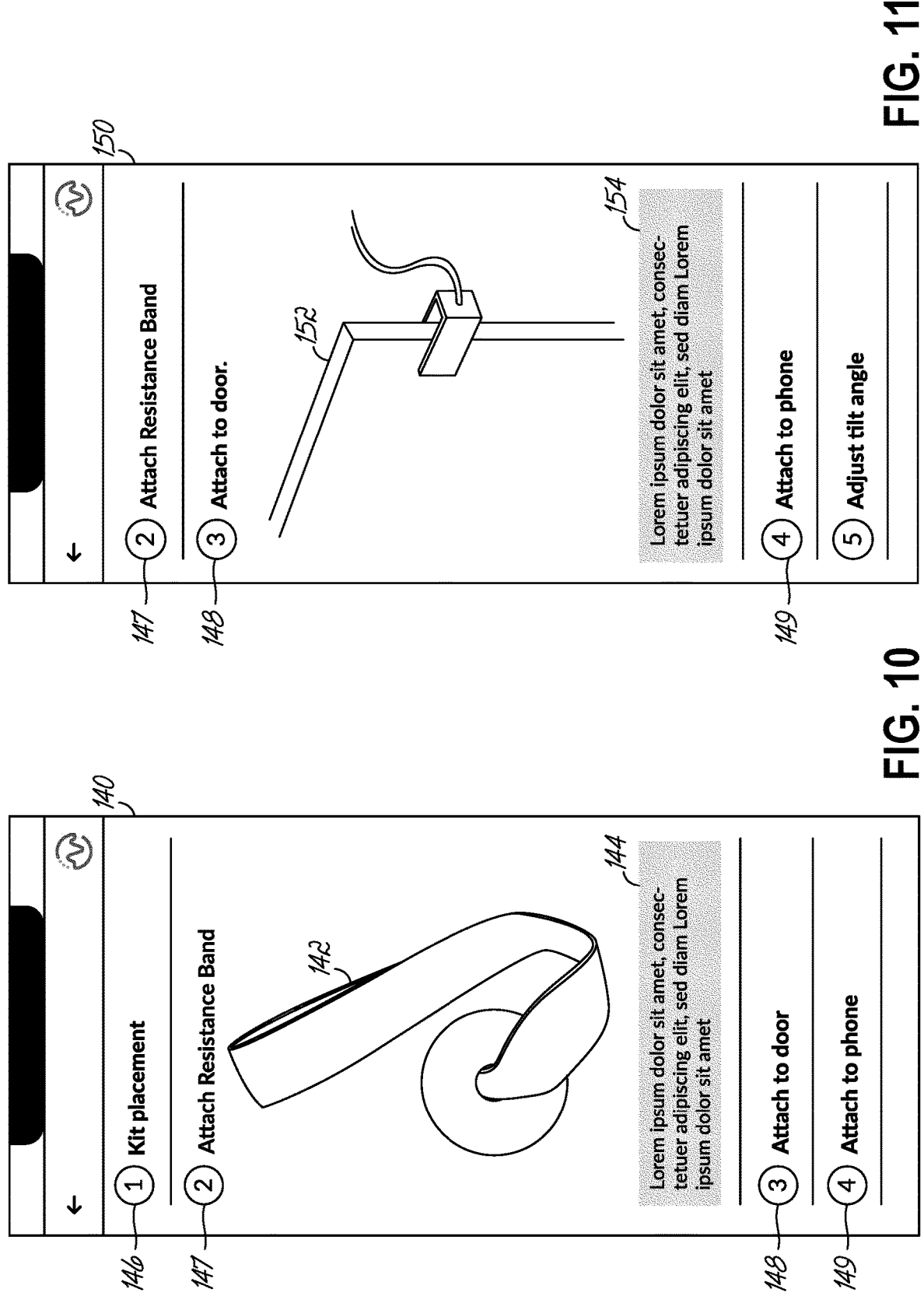

John Fieldman

ACTIVITY | April 13th – April 19th

| | 4/13 MONDAY | 4/14 TUESDAY | 4/15 WEDNESDAY | 4/16 THURSDAY | 4/17 FRIDAY | 4/18 SATURDAY | 4/19 SUNDAY |
|---|---|---|---|---|---|---|---|
| Exercise Name | | | | | | | |
| Exercise Name — Component 1 SUBJECTIVE SLEEP QUALITY | 1 | 2 | 3 | 3 | 3 | 3 | 3 |
| Exercise Name — Component 2 SLEEP LATENCY | 1 | 2 | 2 | 2 | 2 | 3 | 3 |
| Exercise Name — Component 3 SLEEP DURATION | 1 | 2 | 3 | 3 | 3 | 3 | 3 |
| Exercise Name — Component 4 HABITUAL SLEEP EFFICIENCY | 1 | 2 | 2 | 2 | 2 | 3 | 3 |
| Exercise Name — Component 5 STEP DISTURBANCE | 1 | 2 | 3 | 3 | 3 | 3 | 3 |
| Exercise Name — Component 6 USE OF SLEEPING MEDICATION | 1 | 2 | 2 | 2 | 2 | 3 | 3 |
| PSQI — Component 7 DAYTIME DYSFUNCTION | 1 | 2 | 2.5 | 2.5 | 2.5 | 3 | 3 |
| GLOBAL PSQI SCORE | | | | | | | |

SINCE LAST CALIBRATION | BY SESSION | SINCE BEGINNING

FIG. 35

SYSTEM AND METHOD FOR REMOTELY PROVIDING AND MONITORING PHYSICAL THERAPY

CROSS-REFERENCE TO RELATED APPLICATIONS

The present application is a U.S. National Stage entry under 35 U.S.C. § 371 of, and claims priority to, International Application No. PCT/US2022/047066, filed Aug. 26, 2021, which claims the filing benefit of U.S. Provisional Application Ser. No. 63/071,762, filed Aug. 28, 2020, the disclosures of which are incorporated by reference in their entireties.

FIELD OF THE INVENTION

The present invention generally relates to exercise equipment and, in particular, to methods, systems, and computer program products for remotely managing physical therapy and rehabilitation.

BACKGROUND OF THE INVENTION

Existing technology-enabled exercise applications are not well suited to patients receiving physical therapy or rehabilitation. In particular, conventional methods of treatment do not provide an ability to view therapeutic activities completed outside of the clinical environment, such as in the home of the patient. Physical therapists must therefore often make subjective judgements based solely on their professional experience and education. Because out-of-office therapeutic activities constitute about 70% of a typical treatment plan, the lack of the tools to effectively transfer treatment plans from the clinic to the home environment can be an impediment to maintaining compliance. This lack of compliance may, in addition to reducing the effectiveness of the treatment, impede the confidence building between patient and caregiver necessary to achieve consistent outcomes.

Applications used for performing therapeutic exercises outside of a clinical setting are often difficult to use, and the accompanying hardware is often bulky and expensive. In many cases, the applications also require multiple sensors or markers to be placed on different parts of the body. Typical equipment setups include one or more cameras that must be positioned around the workout area. While the patient is exercising, the cameras capture sequences of images of the patient performing the exercise. The system then attempts to determine the patient's movement based on the positions of the optical markers in the images using inverse kinematics.

The complexity inherent in these types of exercise systems often leads to incorrect utilization and inconsistent patient experiences. Using cameras to assess body movement patterns also has several disadvantages. Camera-based systems are typically expensive, and have significant logistical requirements. The need to avoid changes in perceived position due to parallax may contribute to these logistical requirements. The logistical requirements may include the need for a large area in which the cameras can be set up and preferably left undisturbed. The need to attach optical markers to specific parts of the patient's body can further complicate matters, leading to inconsistent measurements between sessions, increased errors, and reduced user compliance. These and other disadvantages of conventional exercise monitoring systems can lead to low adoption rates and utilization.

As a result of the above deficiencies in remote exercise applications and equipment, it has been estimated that when patients undergoing physical therapy are prescribed exercises which are to be performed at home, only 35% of the patients fully adhere to their exercise plan, and 70% drop out after their third visit.

Thus, there is a need for improved systems, methods, and computer program products for facilitating and monitoring exercise sessions in a home environment.

SUMMARY OF THE INVENTION

The present invention overcomes the foregoing and other shortcomings and drawbacks heretofore known in systems, methods, and computer program products for remotely managing exercise regimes. While the present invention will be discussed in connection with certain embodiments, it will be understood that the present invention is not limited to the specific embodiments described herein.

In an embodiment of the present invention, an apparatus is provided. The apparatus includes a human-device interface, a motion sensor operatively coupled to the human-device interface, and a controller. The controller is configured to receive first motion data from the motion sensor and transmit the first motion data to a first computing device. The first computing device displays a first graphical element that depicts a first movement of the human-device interface based on the first motion data.

In an aspect of the present invention, the apparatus may further include a source of resistance.

In another aspect of the present invention, the apparatus may further include a force sensor configured to detect an amount of force being generated by the source of resistance.

In another aspect of the present invention, the human-device interface may include a grip having one or more transducers.

In another aspect of the present invention, the one or more transducers may include at least one of a pressure sensor and a haptic device.

In another aspect of the present invention, the apparatus may further include a network database, and the controller may be configured to transmit the first motion data to the network database.

In another aspect of the present invention, the apparatus may further include a second computing device configured to retrieve the first motion data from the network database and display a second graphical element that depicts the first movement of the human-device interface based on the first motion data.

In another aspect of the present invention, the first computing device may be a patient device, and the second computing device may be a therapist device.

In another aspect of the present invention, the first computing device may be configured to determine a target motion based on the first motion data, receive second motion data indicative of a second movement, determine a current motion based on the second motion data, and compare the current motion to the target motion. In response to the current motion matching the target motion, the first computing device may display a second graphical element indicating an exercise is being performed properly. In response to the current motion not matching the target motion, the first computing device may provide feedback indicating the exercise is not being performed properly.

In another aspect of the present invention, the first computing device may be configured to determine the target motion by receiving a first signal from a therapist device, in response to receiving the first signal, begin recording the first motion data, receiving a second signal from the therapist device, in response to receiving the second signal, stop recording the first motion data, and in response to receiving a third signal from the therapist device, saving the recorded data as calibration data.

In another aspect of the present invention, the first graphical element may depict an animated figure performing the exercise, and a movement of the animated figure may be based on the target motion, the current motion, or both the target motion and the current motion.

In another aspect of the present invention, the first computing device may be further configured to compare the current motion to the target motion. If the current motion does not match the target motion, the first computing device may cause at least a portion of the animated figure to provide feedback indicating that the exercise is being performed improperly, and display a third graphical element that provides feedback indicating how to correct the current motion to match the target motion.

In another aspect of the present invention, the human-device interface may include the grip having the haptic device, and the first computing device may be further configured to, if the current motion does not match the target motion, cause the haptic device to provide feedback indicating that the exercise is being performed improperly.

In another aspect of the present invention, the first computing device may be further configured to, if the current motion does not match the target motion, emit an auditory warning.

In another embodiment of the present invention, a method is provided. The method includes receiving, at the first computing device, the first motion data from the motion sensor operably coupled to the human-device interface, the first motion data indicative of the first movement, and displaying, on the first computing device, the first graphical element that depicts the first movement of the human-device interface based on the first motion data.

In an aspect of the present invention, the method may further include transmitting the first motion data to the network database.

In another aspect of the present invention, the method may further include retrieving, at the second computing device, the first motion data from the network database, and displaying, on the second computing device, the second graphical element that depicts the first movement of the human-device interface based on the first motion data.

In another aspect of the present invention, the method may further include determining the target motion based on the first motion data, receiving the second motion data from the motion sensor indicative of the second movement, determining the current motion based on the second motion data, and comparing the current motion to the target motion. In response to the current motion matching the target motion, the method may display the second graphical element indicating the exercise is being performed properly. In response to the current motion not matching the target motion, the method may provide feedback indicating the exercise is not being performed properly.

In another aspect of the present invention, the method may determine the target motion based on the first motion data by receiving the first signal from the therapist device, in response to receiving the first signal, begin recording the first motion data, receiving the second signal from the therapist device, in response to receiving the second signal, stop recording the first motion data, and in response to receiving the third signal from the therapist device, saving the recorded data as calibration data.

In another embodiment of the present invention, a computer program product is provided. The computer program product includes a non-transitory computer-readable storage medium, and program code stored on the non-transitory computer-readable storage medium. When executed by one or more processors, the program code causes the one or more processors to receive the first motion data from the motion sensor operably coupled to the human-device interface, the first motion data indicative of the first movement, and display the first graphical element that depicts the first movement of the human-device interface based on the first motion data.

BRIEF DESCRIPTION OF THE DRAWINGS

The accompanying drawings, which are incorporated in and constitute a part of this specification, illustrate various embodiments of the present invention and, together with the general description of the present invention given above, and the detailed description of the embodiments given below, serve to explain the embodiments of the present invention.

FIGS. 6-27 are screen shots of a patient application that runs on the patient device of FIG. 1.

FIGS. 28-37 are screen shots of a therapist application that runs on the therapist device of FIG. 1.

Figure 1:
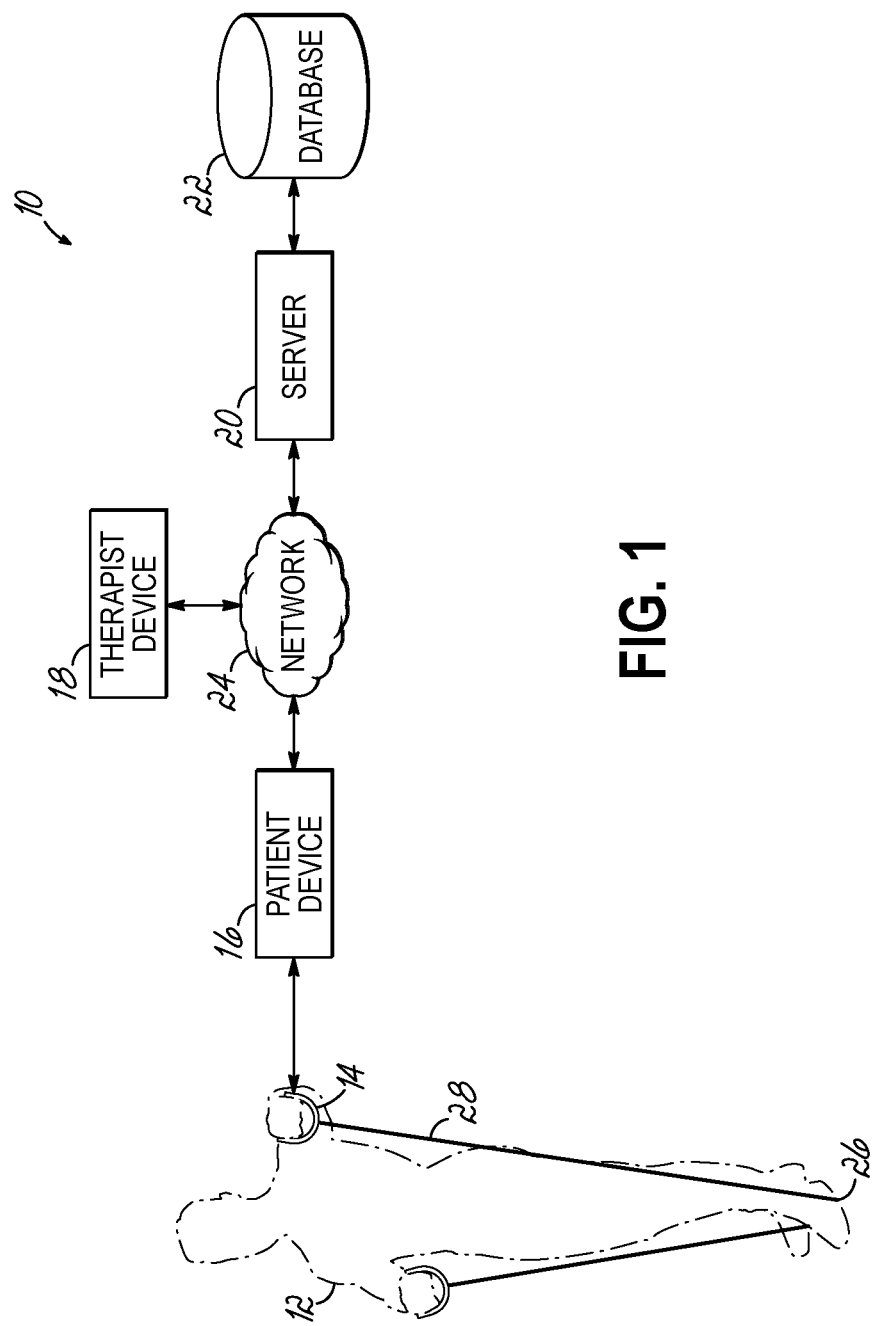
FIG. 1 is a diagrammatic view of an operating environment in accordance with an embodiment of the present invention including a patient device, a therapist device in communication with a server and a database via a network, and an exercise device in communication with the patient device.

It should be understood that the appended drawings are not necessarily to scale, and may present a somewhat simplified representation of various features illustrative of the basic principles of the present invention. The specific design features of the sequence of operations disclosed herein, including, for example, specific dimensions, orientations, locations, and shapes of various illustrated components, may be determined in part by the particular intended application and use environment. Certain features of the illustrated embodiments may have been enlarged or distorted relative to others to facilitate visualization and a clear understanding.

DETAILED DESCRIPTION OF THE INVENTION

Embodiments of the present invention provide a simple and portable system for management of exercise regimens prescribed to patients that are to be carried out in a home environment. Feedback mechanisms may help patients correct their motion during exercise. Asynchronous virtual care may be enabled by allowing patients to complete exercise routines correctly without the need for real-time feedback from a therapist. The system thus addresses an unmet need for personalized care provided in a home environment that is guided by a therapist, that produces higher compliance rates and more consistent outcomes than known methods, and which provides the therapist with objective information with which to assess the treatment plan.

The system includes one or more exercise devices in communication with one or more applications that may be loaded into one or more of a patient device and a therapist device. Data collected from the exercise devices is used to define and monitor patient exercise sessions. Embodiments of the present invention thereby provide a simple, portable, inexpensive, and easy to use solution that extends the in-clinic experience into the home environment of the patient.

Sensors embedded in each exercise device collect data indicative of movement of the exercise device. This motion data is transmitted to an application resident in the patient device, which may be a smartphone or other portable computing device. The motion data is processed by the patient application to determine and evaluate the form and movement of the patient while they are exercising with the exercise device. This processing of motion data may use simulation and visualization techniques in conjunction with objective progress measurements. The patient application may provide a more accurate comparison between current motion and target motion than is typically achieved using inverse kinematics.

This improved accuracy enables both real-time and post-session feedback mechanisms that can help the patient correct their motions, provides objective measures of progress over the course of the therapy, and thereby enables the patient to achieve a greater benefit from the exercise. By embedding motion sensors and supporting circuitry in the exercise device, and transmitting data to the patient device, embodiments of the present invention minimize the burdens imposed by the setup process and logistical needs, and reduce the potential for errors. Advantageously, by facilitating setup and use, embodiments of the present invention may improve adoption, portability, and equipment costs as compared to known systems.

Data received by the patient device may be forwarded to a network database, where it can be accessed by a therapist application. The therapist application may use the data to generate graphical images that facilitate visualization of the patient's movement. Based on this visualization, the therapist can make informed decisions throughout the rehabilitation process without having to see the patient in a clinical environment. This ability to make decisions asynchronously may result in higher quality and quantity of care for each patient's rehabilitation treatment plan.

The system captures kinematic body motions of patients performing exercises, and provides feedback to patients and therapists regarding the performance of the exercises without the need for bulky sensors or cameras. The system thereby extends physical therapy and other treatments involving the performance of exercises by a patient beyond the clinical setting. Data collected by motion sensors embedded in the exercise device may be collectively referred to herein as "motion data". Motion data may include, but is not limited to, data indicative of linear or angular acceleration, velocity, position, orientation, and force. Motion data generated by the exercise device may be received by a patient device (e.g., a smartphone) and forwarded to a network database. The motion data can then be used to generate visual aids that enable therapists to analyze patient movements and progress while outside the clinical environment, and make informed decisions regarding treatment throughout a rehabilitation process. The motion data may also be used to provide visual feedback to the patient while they are exercising, thereby helping the patient maintain form and perform the exercise properly. The system may thereby improve the quality and quantity of care received by the patient outside a clinical environment.

In the clinical environment, the system may be used by the physical therapist to assess the patient, create a treatment plan, and calibrate exercises specific to the patient's physical build and recovery status. In the home environment, the system may be used by the patient to follow guided instructions on their phone or other suitable computing device to complete the prescribed treatment routine. The physical therapist may then evaluate the results and personalize the patient's treatment plan based on motion data relating to the patient's exercise sessions collected by the system.

FIG. 1 depicts an exemplary operating environment 10 in accordance with an embodiment of the present invention. The operating environment 10 may include a patient 12, at least one exercise device 14, a patient device 16, a therapist device 18, a server 20, a database 22, and a network 24. Although the exemplary exercise device 14 is depicted in the form of a handle, it should be understood that embodiments of the present invention are not limited to this type of exercise device 14. Other types of exercise devices 14 that may be used by embodiments of the present invention include ankle weights, head bands or pads (e.g., for neck exercises), resistance devices configured to exercise hip adductors, biceps (elbow flexion), hamstrings (knee flexion), abdominal muscles, back muscles, or any other device that can be worn, held, attached to, or manipulated by the patient 12 during performance of an exercise.

Figure 1A:
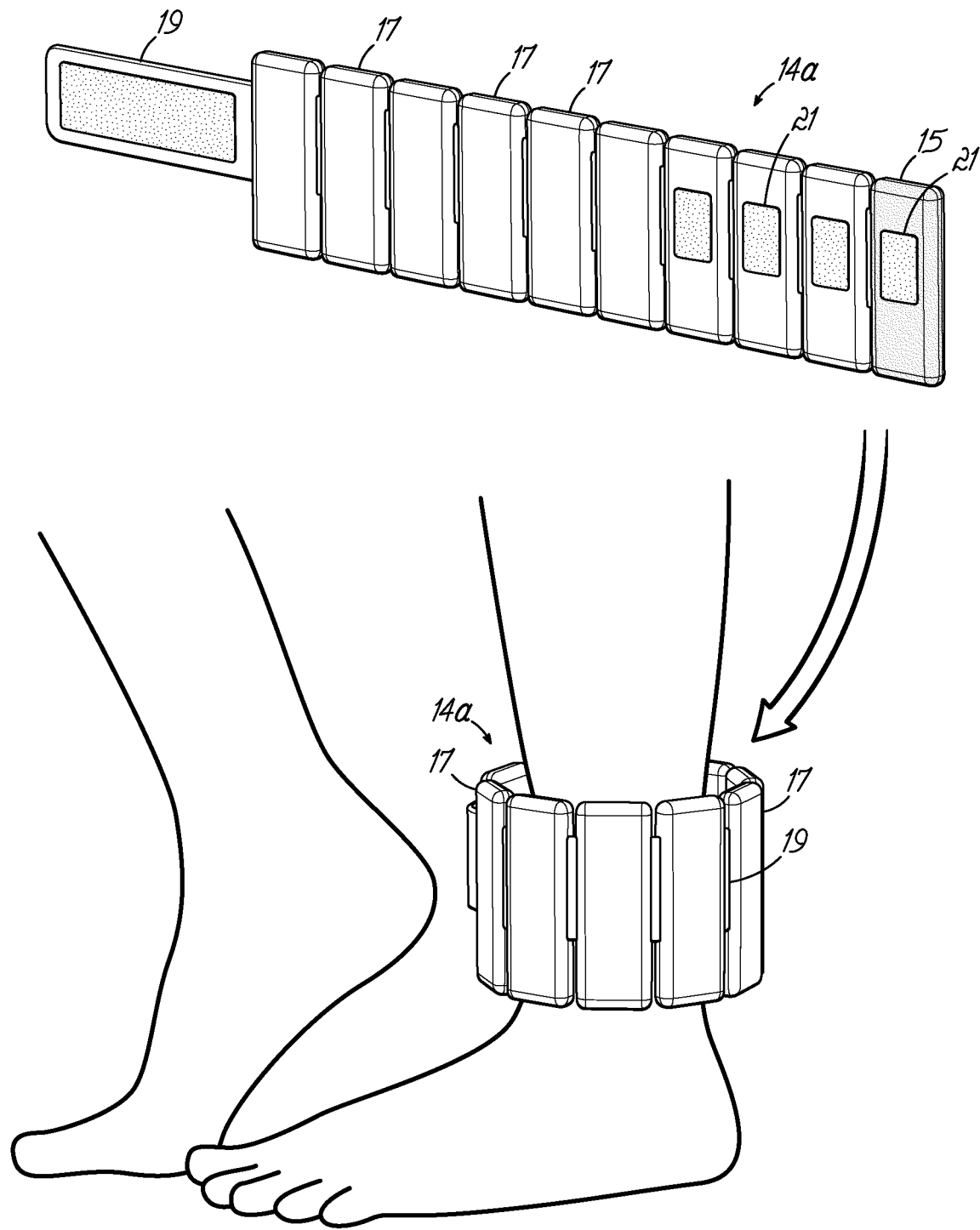
FIG. 1A is a diagrammatic view of an exemplary exercise device in accordance with an alternative embodiment of the present invention.
Figure 2:
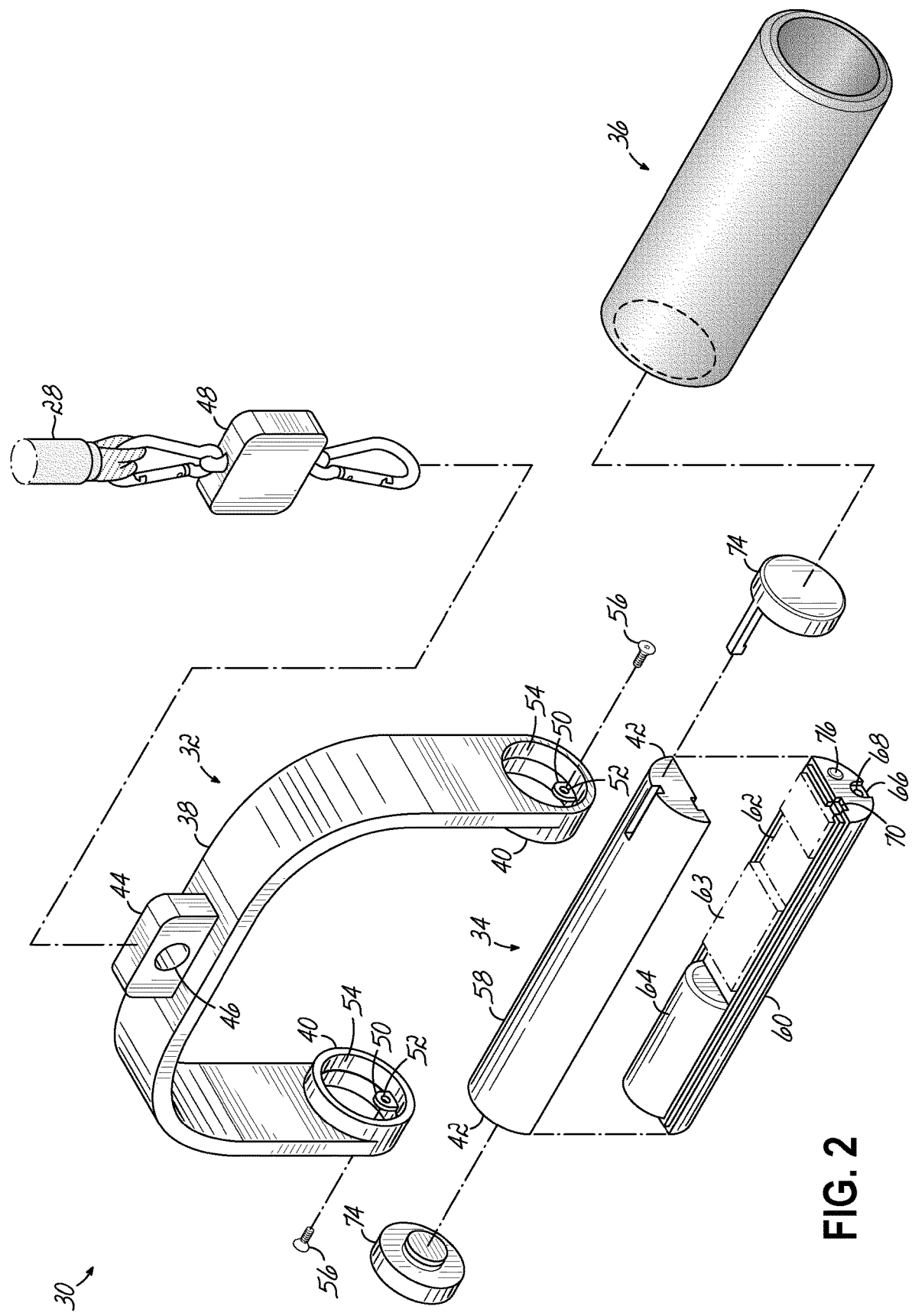
FIGS. 2, 3, and 3A-3F are schematic views showing additional details of exemplary exercise devices.

By way of example, FIG. 1A depicts an exercise device 14a that may be operatively coupled to an ankle of the patient 12. The exercise device 14a may include a sensor module 15 having an internal power supply (not shown), one or more removable weights 17, and a strap 19. One or more of the sensor module 15 and weights 17 may include a fastener 21, such as a hook-and-loop fastener. In use, the patient 12 may slide the sensor module 15 and a prescribed number of weights 17 onto the strap 19, and attach the strap 19 to their ankle as depicted using the fasteners 21. The weights 17 may range from 1-10 pounds each, for example, and may be varied in both weight and number as the patient 12 progresses through their prescribed therapy. The strap 19 may be adjustable based on human factors and ergonomic standards so that the exercise device 14a can be worn comfortably by patients across a large range of shapes and sizes. The sensor module 15 may provide data to the patient device 16 during performance of exercises that enables the patient device 16 to provide real-time biofeedback on the patient's form, pace, range of motion, and exertion.

The patient 12 may use the exercise device 14 to perform an exercise, e.g., by repeating a movement while holding the exercise device 14. The exercise device 14 may include a human-device interface, such as a handle, grip, strap, attachment device, or other suitable element through which the patient physically interacts with the exercise device 14. The exercise device 14 may be operatively coupled to an anchor point 26 or another exercise device 14 (not shown) by an elastic member 28 (e.g., a resistance band) to provide a source of resistance to the exercise device 14. Exemplary anchor points may include the patient's foot (shown), a door anchor, or any other suitable anchor point. In an alternative embodiment of the present invention, the source of resistance may be provided by the mass of the exercise device 14. To this end, the exercise device 14 may be internally weighted or configured to receive weights. Thus, the exercise device 14 may also be used for exercises where the exercise device 14 is untethered, e.g., for exercises that rely on resistance provided by working against the force of gravity, movement through a fluid (e.g., swimming), or any other type of resistance. Exercise devices 14 may also use elastic members in a compressive manner, such as for exercises that require squeezing, gripping, crunches, or other movements by the patient.

The patient and therapist devices 16, 18 may include smart phones, tablet computers, or any other suitable computing devices. The patient device 16 may communicate with the exercise device 14 using a suitable wireless protocol, such as Bluetooth® or a protocol based on IEEE 802.11, i.e., "Wi-Fi". One or more of the patient device 16 and therapist device 18 may receive data from the exercise device 14 relating to one or more of a status or motion of the exercise device 14. The patient and therapist devices 16, 18 may also transmit data to the exercise device 14, such as control messages, software updates, or any other suitable data. The patient and therapist devices 16, 18 may be configured to display information to the patient 12 or therapist that provides feedback relating to the exercise being performed with the exercise device 14. In a home exercise environment, the patient device 16 may be used with a suitable holder so that the display of the patient device 16 is visible to the patient 12 while the patient 12 is performing the exercise.

The server 20 may host one or more server applications, such as a web server, database management server, etc., that enable the patient device 16 and therapist device 18 to store data to and receive data from the database 22. The patient device 16 and therapist device 18 may communicate with the server 20 through the network 24. The network 24 may include one or more local access networks, wide area networks, cellular networks, the Internet, etc., that enable the patient device 16, therapist device 18, and server 20 to exchange data.

FIGS. 2, 3, and 3A-3D depict an exemplary exercise device 14 in the form of a handle 30. The handle 30 includes a loop 32, a housing 34, and a grip 36 that provides a human-device interface. The loop 32 may be made from a semi-rigid material (e.g., nylon or plastic) and include an arcuate band 38 that joins a pair of rings 40 each configured to receive a respective end 42 of the housing 34. A boss 44 may project from the loop 32 and include a hole 46 for coupling the elastic member 28 to the handle 30 using a carabiner or other suitable coupler. The handle 30 may be coupled directly to the elastic member 28, or through an external force sensor 48. In cases where an external force sensor 48 is used, one carabiner or other suitable coupler may be used to couple one side of the force sensor 48 to the handle 30, and another carabiner or other suitable coupler may be used to couple the other side of the force sensor 48 to the elastic member 28. A tab 50 including a hole 52 may project radially inward from an inner surface 54 of each ring 40. Each of the holes 52 may be configured to receive a fastener 56 (e.g., a screw) that operatively couples the loop 32 to the housing 34.

The housing 34 may comprise an upper portion 58 and a lower portion 60 that, when assembled, define a cavity which houses a sensor module 62, an induction coil 63, and a power source 64, e.g., a battery. Each end 42 of housing 34 may include an indentation 66 configured to receive a respective tab 50 of loop 32. Each indentation 66 may include a threaded hole 68 configured to threadedly engage a respective fastener 56. When tightened, the fastener 56 may urge the tab 50 into contact with the indentation 66, thereby operatively coupling the housing 34 to the loop 32. The housing 34 may also include one or more openings 70 that provide access to a charging/communication port, e.g., a Universal Serial Bus (USB) port, configured to receive a connectorized cable 72. End caps 74 may be removably coupled to the loop 32 by insertion into the rings 40 to conceal the ends 42 of housing 34. One or more of the end caps 74 may be configured to pivot upward to reveal the charging/communication port and a pressure sensitive device 76 (e.g., a button) that allows the patient to interact with the sensor module 62. Patent interactions using the pressure sensitive device 76 may include turning the sensor module 62 on and off, pairing the handle 30 with the patient or therapist device 16, 18, or any other suitable interaction. The grip 36 may be configured to receive the housing 34 prior to insertion of the ends 42 of housing 34 into the rings 40 of loop 32, and may be configured to rotate about a longitudinal axis of the housing 34.

The grip 36 may have a round or elliptical cross-sectional shape specific to human factors and ergonomics standards for patients spanning a 5% female to 95% male size model. The grip 36 may have an inner diameter of about one inch and a thickness of between 0.15 to 0.25 inches. In an embodiment of the present invention, the grip 36 may include one or more transducers, such as pressure sensors (not shown) or haptic devices. The pressure sensors may enable one or more of the exercise device 14 and the patient device 16 to determine whether the exercise device 14 is being held in the right or left hand of the patient 12, e.g., by identifying thumb placement. The haptic devices may be used to provide haptic feedback to the patient 12, e.g., to indicate to the patient that their form needs correction. Haptic devices may include, for example, a vibration motor or linear resonant actuator that provides the user with instant feedback. This feedback may provide an indication when the user is in a correct position (e.g., at the start of an exercise), and may also be used to let the user know when they have reached the end of an exercise repetition or a target displacement. Auditory feedback may also be used during exercise sessions, either alone or in conjunction with the haptic feedback, to let the user know whether they are tracking at the correct velocity.

Figure 3:
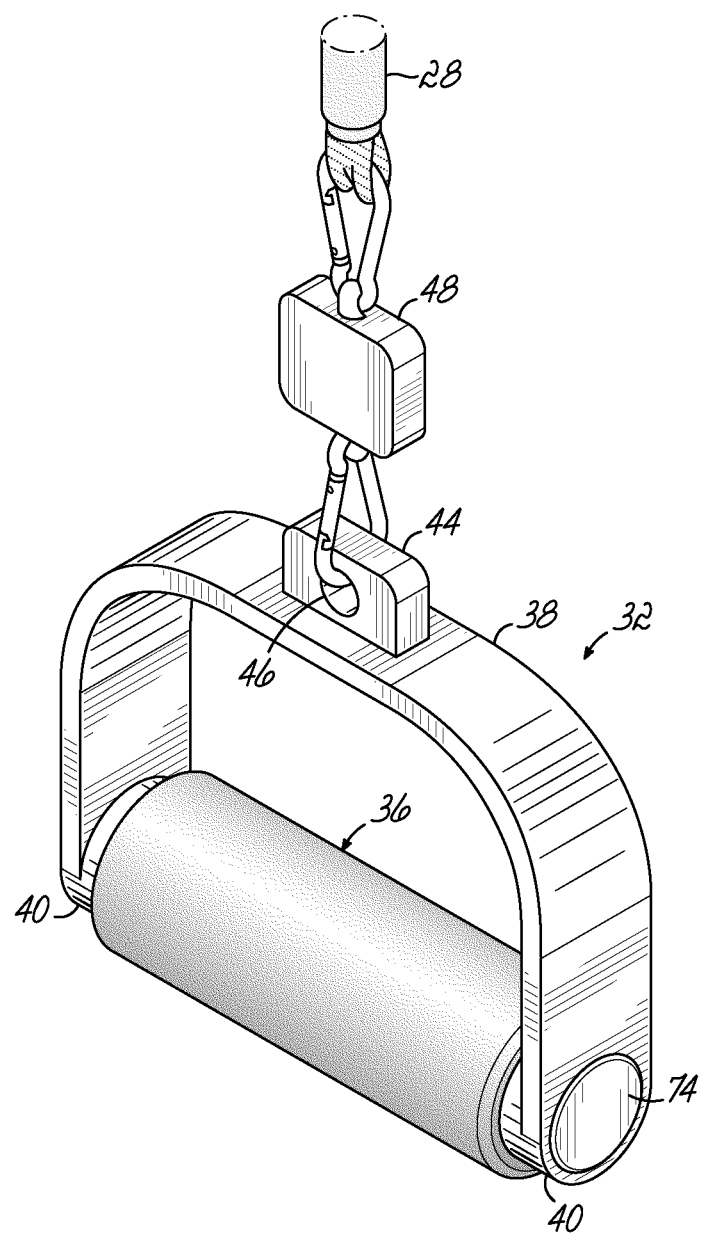
Figure 3A:
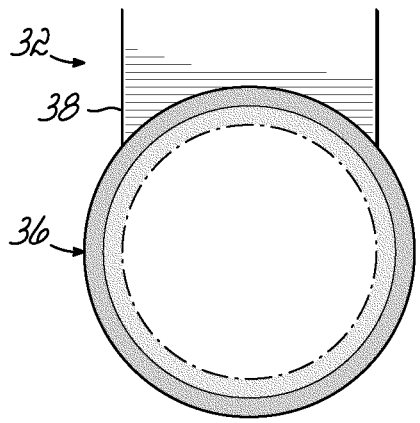
Figure 3B:
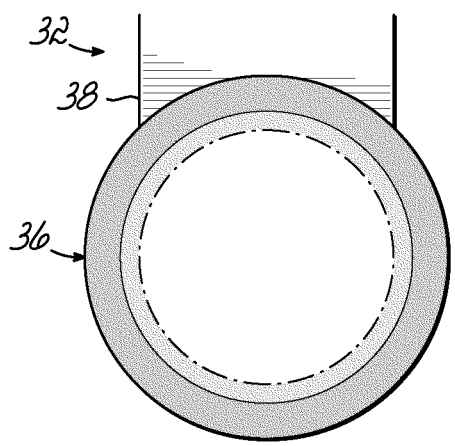
Figure 3C:
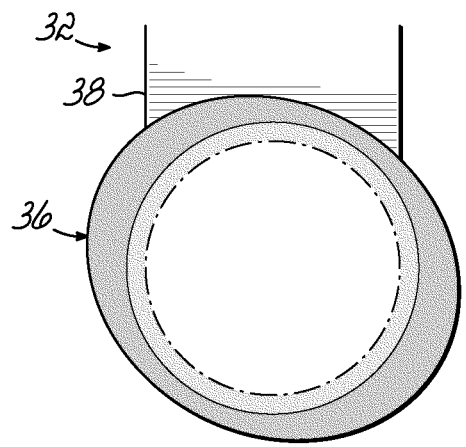
Figure 3D:
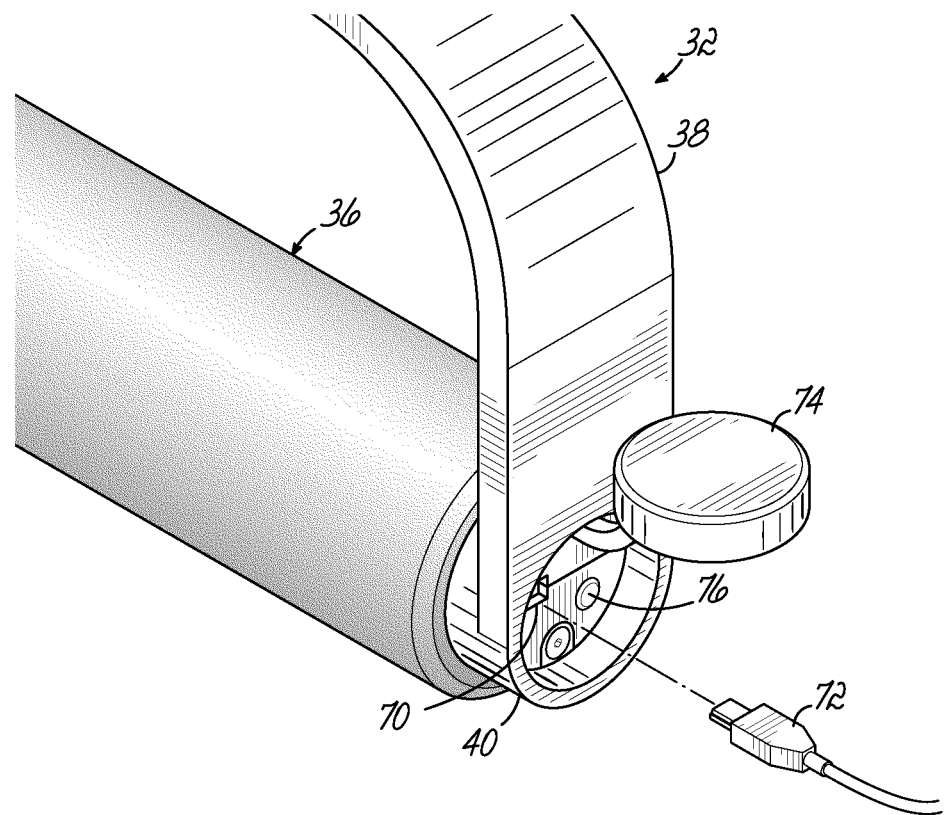
Figure 3E:
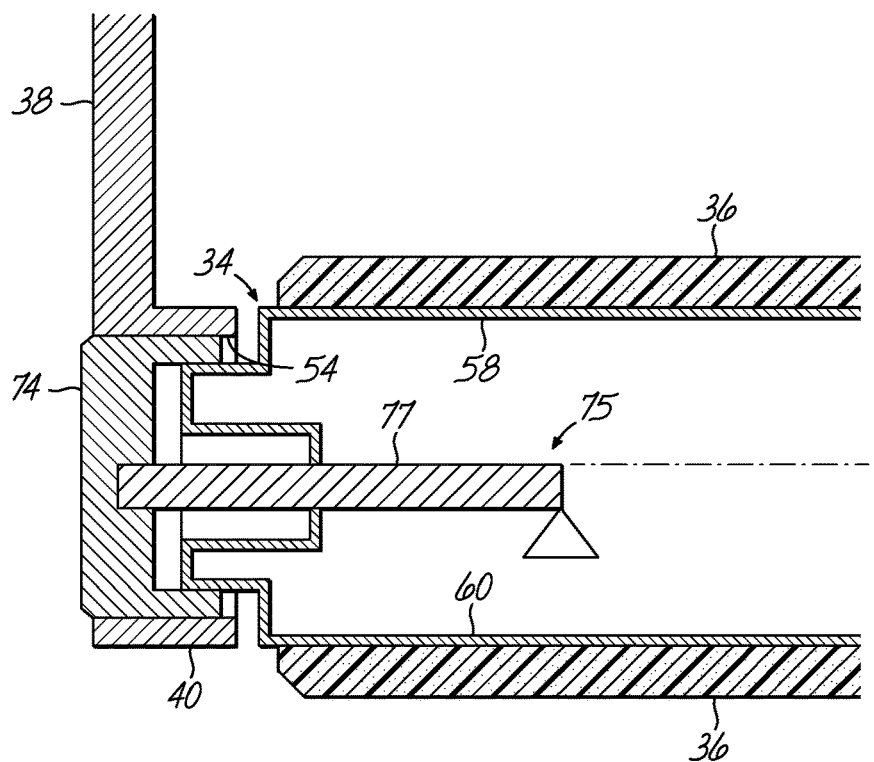
Figure 3F:
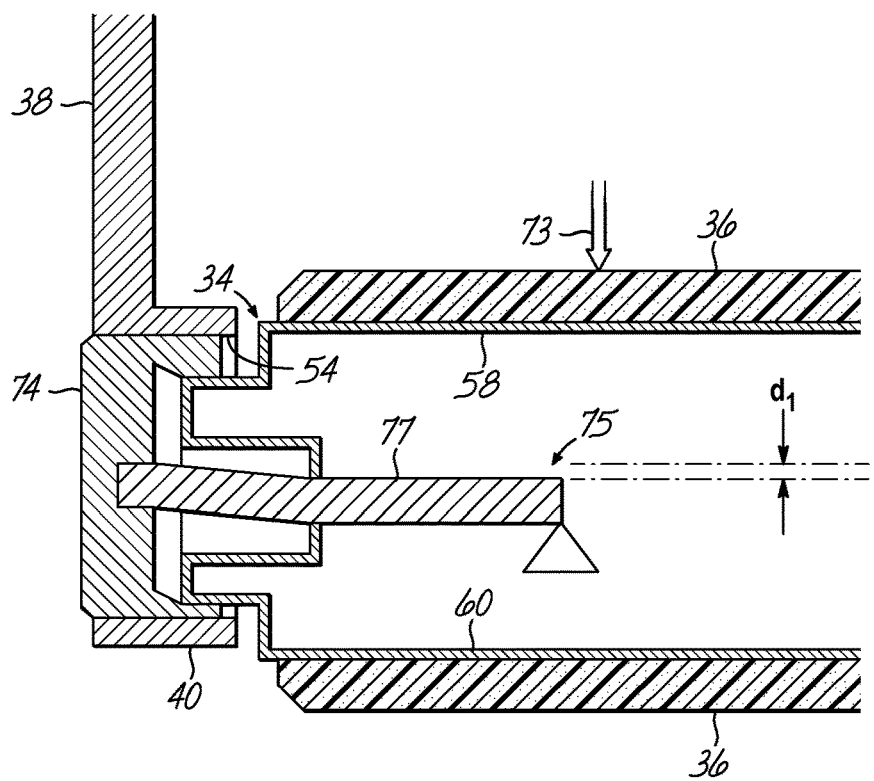

FIGS. 3E and 3F present a cross-sectional view of a portion of the handle 30 in accordance with an alternative embodiment of the present invention. FIG. 3E depicts the handle 30 in a relaxed state, and FIG. 3F depicts the handle 30 while a force 73 is being applied to the grip 36. The housing 34 may be operatively coupled to the rings 40 of loop 32 by an elastic member, e.g., a portion of the end caps 74, a rubber O-ring (not shown), or any other suitable elastic member. The force 73 may cause the housing 34 of handle 30 to compress the elastic member such that the housing 34 is displaced relative to the loop 32 by a displacement distance di. The elastic member may be configured so that displacement distance di is proportional to the magnitude of the applied force 73.

An internal force sensor 75 may be operatively coupled between the housing 34 and one of the rings 40 of loop 32 (e.g., by an end cap 74) so that the force sensor 75 is deformed in response to displacement of the housing 34 relative to the rings 40. The force sensor 75 may include a flex sensor 77 having a flexible insulating substrate that supports a conductive pattern. The electrical resistance of the conductive pattern may change in response to deformation of the flex sensor 77 so that the electrical resistance of the flex sensor 77 depends on the displacement distance di. The magnitude of the force 73 may then be determined based on this electrical resistance.

Figure 4:
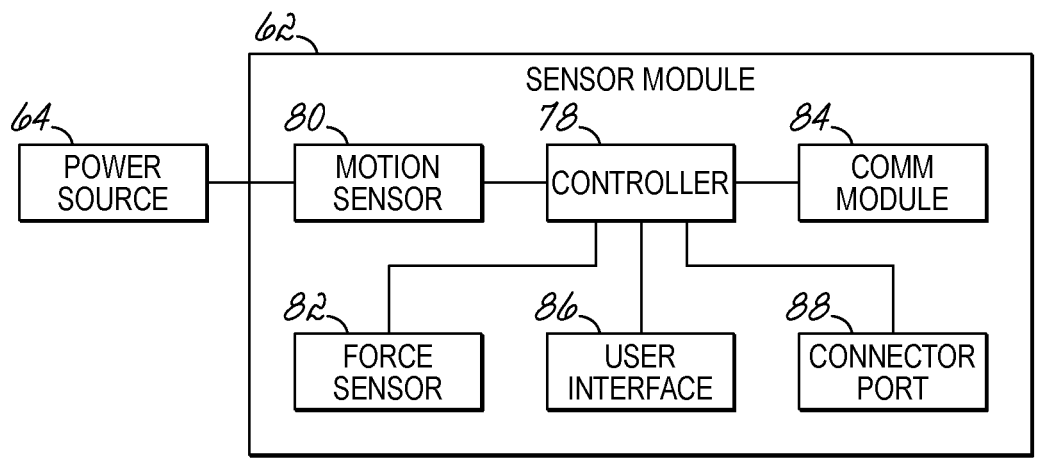
FIG. 4 is a diagrammatic view of a sensor module of the exercise device of FIGS. 2-3D.

FIG. 4 depicts an exemplary sensor module 62. The sensor module 62 may be operatively coupled to the power source 64, and include a controller 78 operatively coupled to one or more of a motion sensor 80, an integrated force sensor 82, a communication module 84, a user interface 86, and a connector port 88. The controller 78 may comprise a microcontroller or other computing device configured to control the sensor module 62. For embodiments of the present invention including an external force sensor 48, the sensor module 62 may receive force data from the external force sensor 48 over a suitable wireless link, such as Bluetooth. In an alternative embodiment, the force data may be received from the external force sensor 48 by the patient device 16, and added to the data received from the sensor module 62.

The motion sensor 80 may include one or more sensors configured to detect the position, movement, or orientation of the handle 30. Exemplary sensors that may be used to quantify kinematics of the handle 30 may include, but are not limited to, time of flight, infrared, or ultrasonic sensors (e.g., to determine position and orientation relative to the surrounding environment), ultra-wideband (UWB) sensors, accelerometers, gyroscopes, magnetometers, or any other type of sensor that can be used to determine the acceleration, velocity, position, or orientation of the handle 30. Accelerometers may be used to measure acceleration along one or more orthogonal axes, e.g., x, y, and z-axes of a cartesian coordinate system. The detected acceleration may be used to determine changes in position and velocity of the exercise device 14. The detected acceleration may also be used determine the direction of gravitational pull in order to detect orientation or tilt. One or more gyroscopes may be used to measure angular movement about the orthogonal axes. Magnetometers may be used to sense magnetic force, such as the magnetic field of the Earth, and can thus be used to orient the exercise device 14 to magnetic north. The data output by the accelerometers, gyroscopes, and magnetometers may be used to determine the position and orientation of the exercise device 14 with respect to Earth or any other suitable frame of reference, such as the patient 12 or another exercise device 14.

In an embodiment of the present invention, the motion sensor 80 may include a six degree-of-freedom motion detector that provides the controller 78 with data indicative of linear motion along, and angular rotation about, three orthogonal axes. This type of motion sensor is sometimes referred to as an Inertial Measurement Unit (IMU). Methods for determining position and orientation using inertial sensors are disclosed by U.S. Pub. No. 2018/0056128 to Bharath Narasimha Rao et al., and U.S. Pat. No. 9,273,967 to Yimei Ding et al., the disclosures of which are incorporated by reference herein in their entireties.

In scenarios in which two or more exercise devices 14 are used, accelerometer, gyroscope, or magnetometer sensors in one exercise device 14 may provide orientation and displacement in space relative to an IMU in another of the exercise devices 14. Orientation and displacement may, in turn, be used to determine rotation and translation of the exercise device 14 relative to the Earth frame. Accelerometers and gyroscopes may be used to measure relatively fast movements (e.g., exercise repetitions), and induction coil/magnetometer sensors may be used to measure slow movements, determine absolute starting position, and determine distances between multiple exercise devices 14.

IMUs may suffer from drift and have poor signal to noise ratio when dealing with low acceleration movements, such as under quasi-static conditions. To mitigate these issues, embodiments of the present invention may leverage IMUs in combination with other sensors for static measurements. Sensors which may be used to improve static measurements may include time of flight sensors, ultrasonic sensors, UWB sensors, or other wireless location tracking technologies, such as Bluetooth Low Energy (BLE). An induction coil in conjunction with a magnetometer may also be used to measure both distance and orientation. Use of these sensors may allow the exercise device 14 to determine its starting position and orientation in cases where quasi-static or static exercises are used as part of a prescribed exercise regime.

The force sensor 48, 75, 82 may include a strain gauge or other device that provides a signal to the controller 78 indicative of an amount of force that is being exerted by the source of resistance (e.g., the elastic member 28) on the exercise device 14. In an embodiment of the present invention, the force sensor 48, 75, 82 may comprise a force sensing resistor (e.g., a polymer thick film (PTF) device) that exhibits a change in resistance (e.g., a decrease in resistance) in response to an increase in force applied to its surface. The force sensing resistor may be positioned between the housing 34 and loop 32, between the housing 34 and grip 36, between the exercise device and elastic member 28, or in any other location through which force is transmitted from the patient 12 to the source of resistance during use of the exercise device 14.

The force sensor 48, 75, 82 may enable the system to directly and accurately measure the force exerted by the patient during each repetition regardless of the position of the exercise device 14. The force sensor 48, 75, 82 may also facilitate self-calibration, resulting in more accurate measurements, and provide a mechanism for assessing the condition of the elastic member 28. For example, if the measured force for a given position of the exercise device 14 differs from an expected value for the elastic member 28, the patient device 16 may indicate that the elastic member 28 should be replaced (e.g., is worn out) or that an elastic member 28 having an incorrect resistance level is being used for the exercise in question.

The communication module 84 may include a wireless transceiver that enables the controller 78 to communicate with external devices (e.g., the patient device 16) using a suitable wireless communication protocol, e.g., a Near Field Communication (NFC) protocol, a Bluetooth or Bluetooth Low Energy (BLE) protocol, and/or Wi-Fi. The communication module 84 may thereby enable the controller 78 to transmit data to, and receive data from, the patient device 16. In cases where more than one exercise device 14 is being used for an exercise (e.g., two exercise devices 14 connected by the elastic member 28), the exercise devices 14 may communicate with the patient device 16 through a single data stream.

The user interface 86 may include one or more input devices (e.g., pressure sensitive device 76) that enable the patient to control or otherwise communicate with the exercise device 14, and one or more output devices (e.g., light emitting diodes) that provide information to the patient 12 (e.g., a power-on indication). For example, in response to the application of pressure to a pressure sensitive device, the exercise device 14 may power up, begin a calibration sequence, establish a communication link with the patient device 16 (e.g., Bluetooth pairing), or any other suitable response. In an alternative embodiment of the present invention, the user interface 86 may include the motion sensor 80, in which case the exercise device 14 may be configured to respond to detection of certain specific types of motion, e.g., shaking or swiping.

The connector port 88 may provide a physical connection for use in charging the power source 64 or uploading and downloading data to and from the controller 78. To this end, the connector port 88 may include one or both of a data and a power connection, such as a USB port. The connector port 88 may also include an inductive or capacitive coupling device configured to enable wireless charging of the power source 64.

Figure 4A:
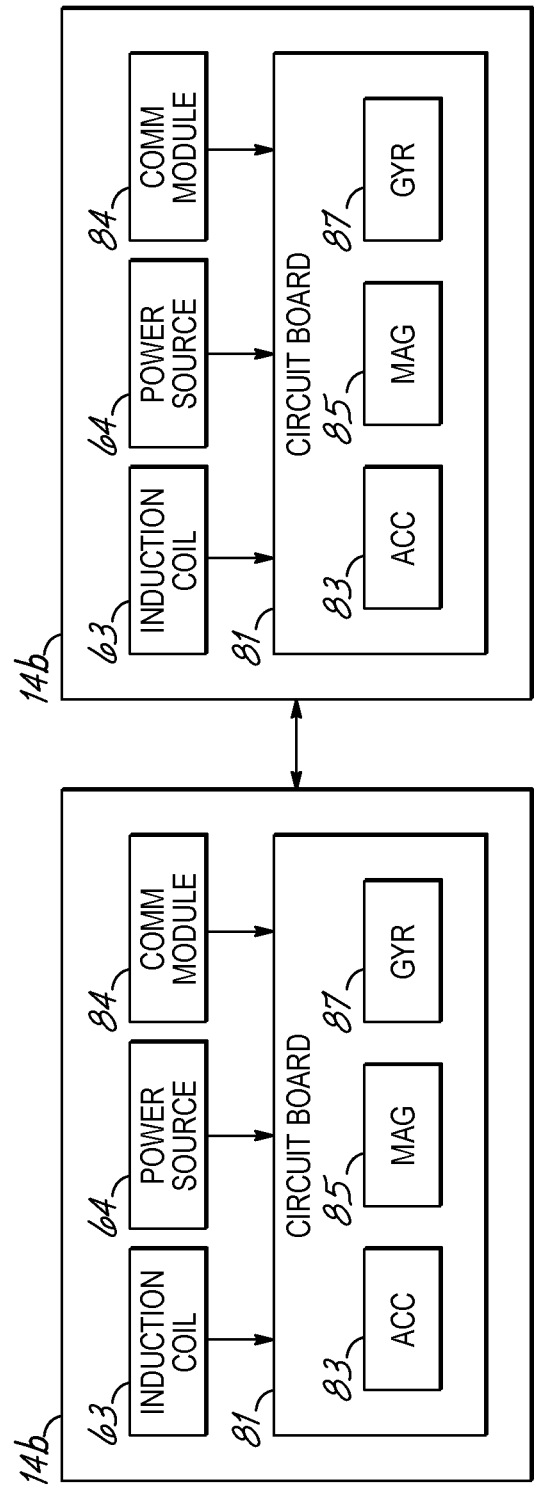
FIG. 4A is a diagrammatic view of a paired set of exercise devices.

FIG. 4A depicts a pair of exemplary exercise devices 14b being used together, e.g., one for each hand. Each of the exercise devices 14b may include the induction coil 63, power source 64, force sensor 82, communication module 84, and a custom circuit board 81. The circuit board 81 may include an accelerometer 83, magnetometer 85, and a gyroscope 87. The circuit board 81 may be configured to determine one or more of the position, orientation, velocity, acceleration, displacement, absement, and the like, of the exercise device 14b based on signals received from the induction coil 63, accelerometer 83, magnetometer 85, and gyroscope 87. The exercise devices 14b may be in communication with each other, and one or more of the patient device 16, the therapist device 18, and the server 20. This communication may be through a suitable communication protocol, such as Bluetooth, and may occur as needed to provide the functions and features described herein. The accelerometer 83, magnetometer 85, and gyroscope 87 in each of the exercise devices 14b may provide orientation and translation in space relative to the IMU in the other exercise device 14b. The induction coil 63 and magnetometer 85 may work together to measure slow movements, determine an absolute starting position, and determine distances between the exercise devices 14b.

During an in-person physical therapy session, the exercise device 14 and therapist device 18 may be in operable communication so that the therapist device 18 receives motion data from the exercise device 14. While the patient is performing an exercise, the therapist may start and stop a process that records the output of each exercise device 14 for use in generating calibration data. The therapist may thereby selectively capture motion data indicative of proper performance of the exercise by the patient. The motion data captured may be used to generate metrics that quantify form, pace, range of motion, and exertion by the patient while performing the exercise. This calibration data may then be used to determine whether the patient is performing the exercise correctly during exercise sessions performed at home, as well as to quantify changes in the patient's range of motion and other physical characteristics over time. Advantageously, calibrating the exercise to the patient in the above manner may allow for improved design and monitoring of rehabilitation regimens, and thus greater personalization according to how far the patient has progressed in their treatment.

Figure 5:
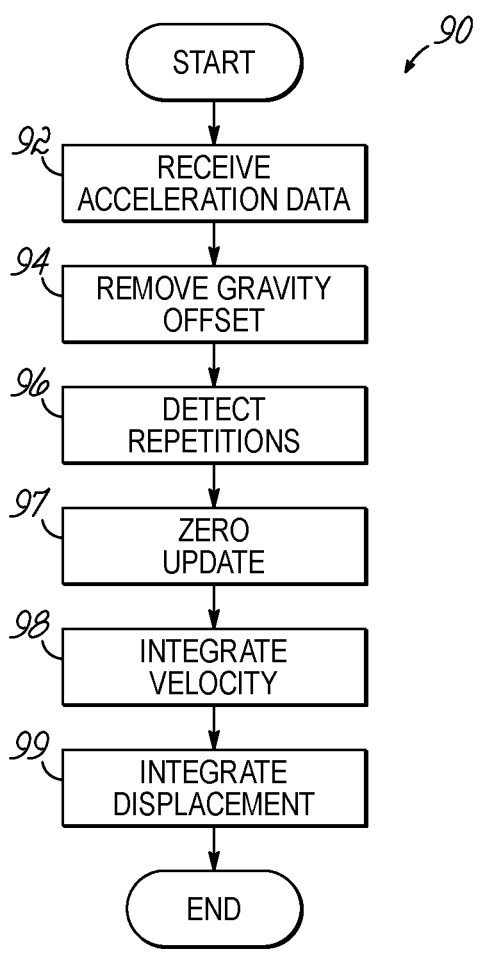
FIG. 5 is a flowchart depicting a process that may be executed by one or more of the patient device, therapist device, exercise device, network, server, or database of FIG. 1.

FIG. 5 depicts a process 90 that may be executed by one or more of the exercise device 14, patient device 16, therapist device 18, server 20, database 22, network 24, or any other suitable computer to process sensor data and generate output metrics. In block 92, the process 90 may receive raw acceleration data, e.g., from the motion sensor 80. In response to receiving the acceleration data, the process 90 may proceed to block 94 and remove a fixed offset due to gravity. The gravity offset may be removed from the acceleration data, for example, by using a Kalman filter.

In block 96, the process 90 may detect repetitions of a prescribed movement. To detect a repletion, the process 90 may determine an orientation of the one or more exercise devices 14 being used. If there is more than one exercise device 14 being used, the process 90 may also determine one or more distances between the exercise devices 14. Orientation of the exercise device 14 may be determined by measuring the gravity vector, and the distance between exercise devices 14 may be determined using time-of-flight measurements, for example. In response to one or more of the orientation(s) and distance(s) between the one or more exercise devices 14 matching a baseline value associated with an exercise, the process 90 may determine that the user is at the start of a repetition of the exercise.

In block 97, the process may perform a zero velocity update. Zero velocity updates may be performed each time the process 90 determines the exercise device 14 is in a zero velocity condition. A zero velocity condition may be determined, for example, based on the magnitude of total acceleration (e.g., when total acceleration $a_{TOTAL}=1$ G), a moving acceleration variance, magnetometer measurements, the magnitude of gyro signals, or any other suitable method. The process 90 may detect the start and the end of a zero velocity condition by comparing collected data with one or more predetermined thresholds.

While in the zero velocity condition, the process 90 may presume any nonzero output of the motion sensor 80 is an error signal, and zero out those velocity measurements. The process 90 may also remove any gyro sensor drift in each of on or more channels. Zero velocity conditions may occur when the user ceases movement, such prior to the start of an exercise session, after stopping the exercise session, or momentarily during an exercise session when the exercise device reverses direction. To avoid discontinuities in the measurement function, any errors detected during a zero velocity condition may be propagated backward to a previous zero velocity condition to provide smooth measurement data.

The start of a repetition may be indicated by a rate of change in the output of motion sensor 80 increasing above a threshold level. In response to detecting the start of a repetition, the process 90 may determine and store kinematic movement (e.g., orientation and translation) of the exercise device 14. A Kalman filter may be used to determine the orientation of the exercise device 14 and the orientation of the gravity vector. The gravity vector may be removed from the acceleration data to isolate acceleration due to movement of the exercise device 14. The acceleration due to movement may then be filtered and integrated with respect to time to determine the velocity of the exercise device 14.

In block 98, the process 90 may integrate the velocity of the exercise device 14 with respect to time to determine its displacement. This displacement may be used to determine the position of the exercise device 14, which, in combination with orientation, may be used to determine translation and rotation of the user.

In block 99, the process 90 may integrate displacement with respect to time to determine the absement of the exercise device 14. Absement is a measure of sustained displacement of an object from and initial position, and may be a parameter of the exercise in cases where the user has been instructed to move the exercise device 14 at a certain rate, or hold a certain position for a certain amount of time.

During home exercise sessions, data generated by the sensor module 62 may be transmitted from the exercise device 14 to the patient device 16, either in raw form or after being processed by the controller 78. This data may be used to provide real-time feedback to the patient 12 while they are performing the exercise, e.g., by comparing current motion data to the calibration data. Data collected during home exercise sessions may also be transmitted from patient device 16 to the server 20 for storage in the database 22. The database 22 may also store data that defines a library of exercise movements for use in designing exercise sessions.

Data stored in the database 22 may be used to generate output that can be viewed by physical therapists to monitor patient progress between in-person visits. The ability to monitor progress of patients between in-person sessions may allow therapists to identify unexpected problems or progress early on, and adjust treatment regimens midcourse if indicated. The increased level of engagement between the patient and the therapist provided by embodiments of the present invention may essentially extend the therapist into the patient's home. This may both reduce the need for frequent in-person visits and result in improved compliance with prescribed exercise regimes and patient care.

Patient Application

Embodiments of the present invention may include a patient application resident on the patient device 16. The patient application may provide the patient with a prescribed treatment and exercise regimen, instructions for the correct approach and technique for each exercise based on their personalized in-clinic experience, real-time feedback to help correct technique where necessary, metrics to help the patient understand their progress relative to their goals, and a personalized exercise and session-specific notifications to assist the patient over the course of their treatment.

To this end, the patient application may cause the patient device 16 to display graphical elements depicting movement of the patient (e.g., an animated figure), as well as other graphical elements that demonstrate the pace, range of motion, form, and exertion of the patient in real-time as the patient is performing an exercise. To provide realistic movement, animated figures may be generated, for example, by a human body movement simulator based on the motion data. The graphical elements may demonstrate how to perform the exercise by comparing the current motion data to calibration data generated during an in-clinic therapy session. By providing immediate feedback and guidance, the patient application may improve compliance with the exercise regimen and the accuracy with which the patient performs the prescribed exercises.

Figure 6:
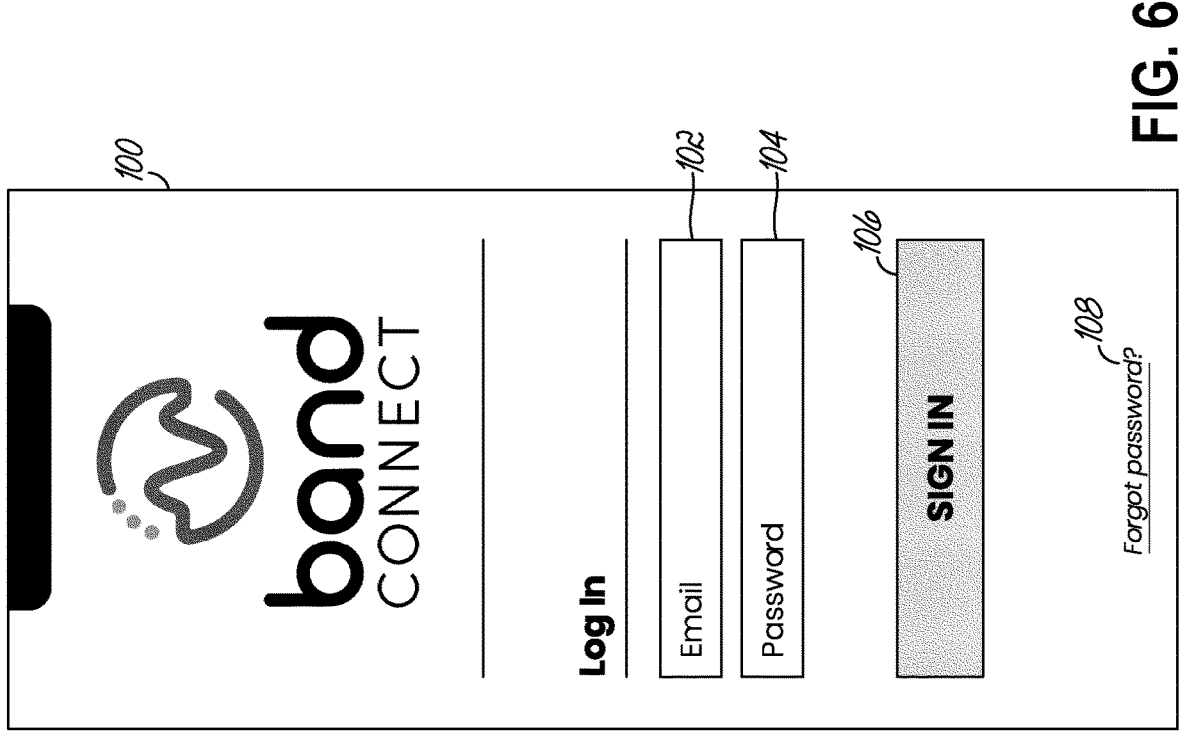

Referring now to FIG. 6, the patient 12 may begin an exercise session by launching an application on the patient device 16. Exercise sessions may include one or more exercise sets, with each exercise set comprising a number of repetitions of an exercise. The patient 12 may launch the application, for example, by activating an application icon displayed by the patient device 16. In response to launching the application, the patient device 16 may display a login screen 100. The login screen 100 may include a data entry field 102 for a patient identifier (e.g., the patient's email address), a data entry field 104 for a password, and a control element 106 (e.g., a "sign in" button) for signing into the application. Activating the control element 106 of login screen 100 may cause the application to check the patient's identity and password. The application may prevent access to data relating to the patient's treatment regimen unless the patient 12 can provide valid login information. The login screen 100 may include an additional control element 108 that can be activated by the patient 12 to launch a password/patient identifier recovery process if the patient 12 has forgotten their login information.

Figure 7:
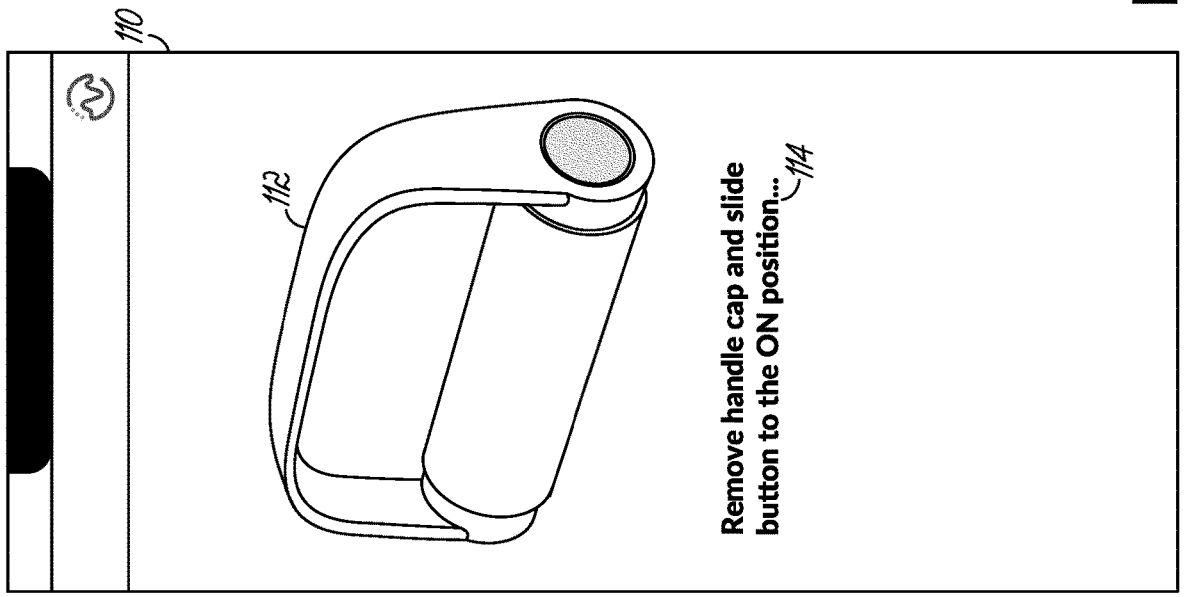

In response to the application confirming the patient's login information, the patient device 16 may display an instruction screen, such as the exemplary instruction screen 110 depicted by FIG. 7. The instruction screen 110 may include a graphical element 112 depicting the exercise device 14 and a data display field 114 that provides instructions for using the exercise device 14, e.g., instructions for powering up the exercise device 14, causing the exercise device 14 to pair with the patient device 16, or any other suitable instructions. The application may store data in memory that records whether the patient 12 has logged in or otherwise used the application before, and select the type of screen to display based on the patient's history with the application.

Figure 8:
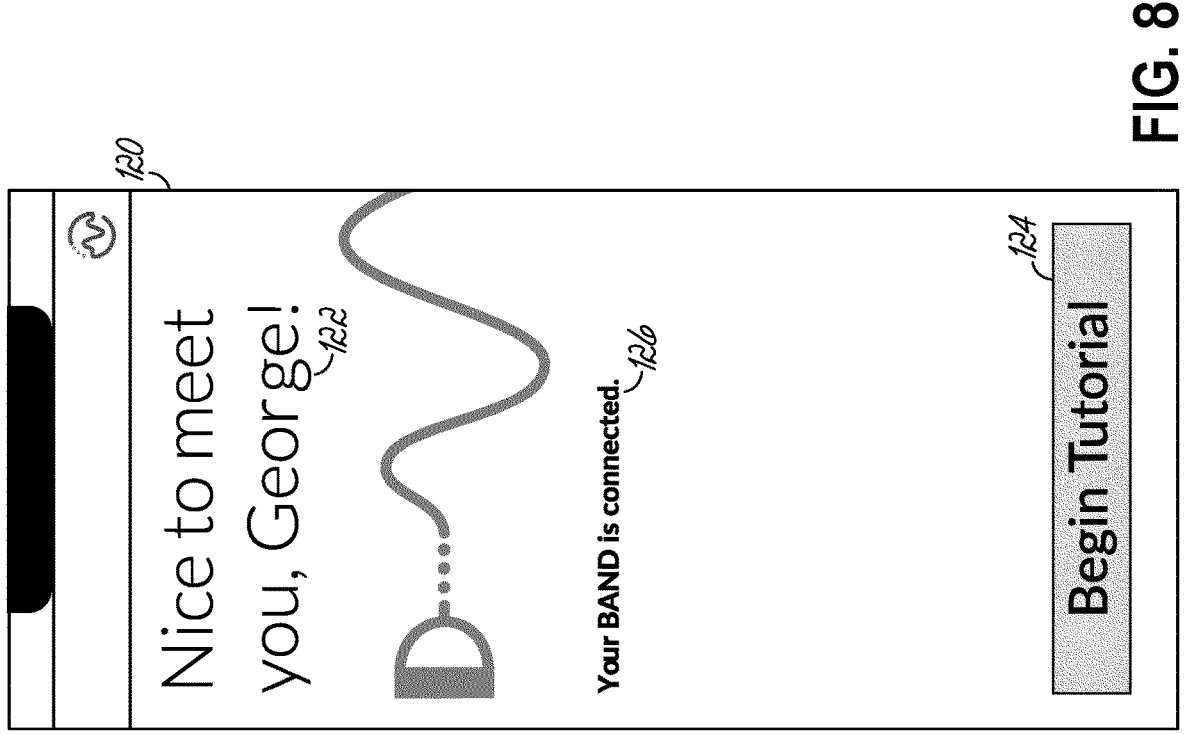

Referring now to FIG. 8, if the patient 12 is logging into the application for the first time, the application may cause the patient device 16 to display an exemplary first-time patient welcome screen 120. The welcome screen 120 may include a graphical element 122 which displays a greeting (e.g., "Nice to meet you, George!"), and a control element 124 (e.g., a "Begin Tutorial" button) appropriate for a first-time patient 12. The welcome screen 120 may also include a data display field 126 that provides information to the patient 12, such as the status of a connection to one or more exercise devices 14.

Figure 9:
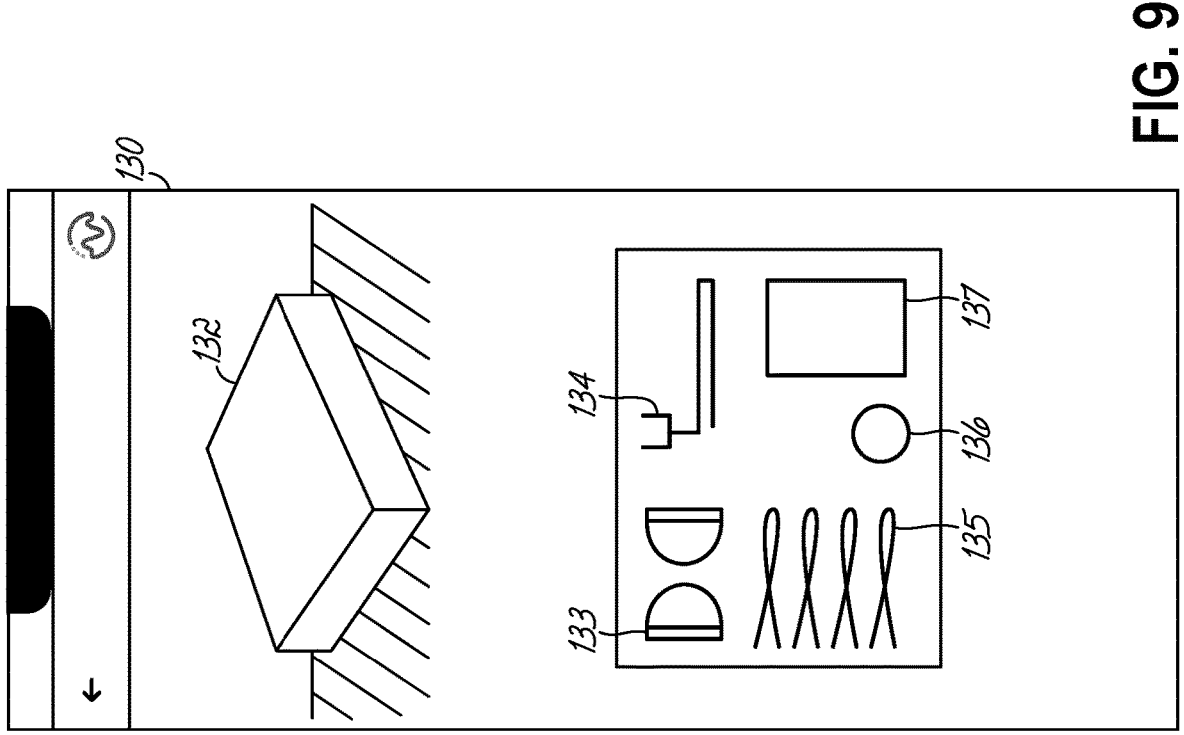

In response to the patient 12 activating the control element 124, the application may cause the patient device 16 to display pre-session set-up screen, such as the exemplary kit explanation screen 130 depicted in FIG. 9. The kit explanation screen 130 may include one or more graphical elements 132-137 depicting the components included in an exemplary exercise device kit. The graphical elements 132-137 may include a graphical element 132 depicting the container the kit came in, as well as graphical elements 133-137 depicting one or more exercise devices 14 (e.g., two exercise devices), a holder for the patient device 16, one or more elastic members, a door anchor, and an instruction guide, respectively. These graphical elements may instruct the patient how to set up their home environment prior to beginning their treatment sessions.

As the tutorial continues (e.g., in response to the patient 12 proceeding to additional screens), the application may cause the patient device 16 to display an instruction screen, such as the exemplary instruction screen 140 depicted by FIG. 10. The instruction screen 140 may include a graphical element 142 depicting a component of the kit (e.g., an elastic band and door anchor) and a data display field 144 that provides written instructions for setting up the depicted component. The instruction screen 140 may also include one or more control elements 146-149 that enable the patient 12 to advance to the next instruction screen or return to a previous instruction screen.

Figure 12:
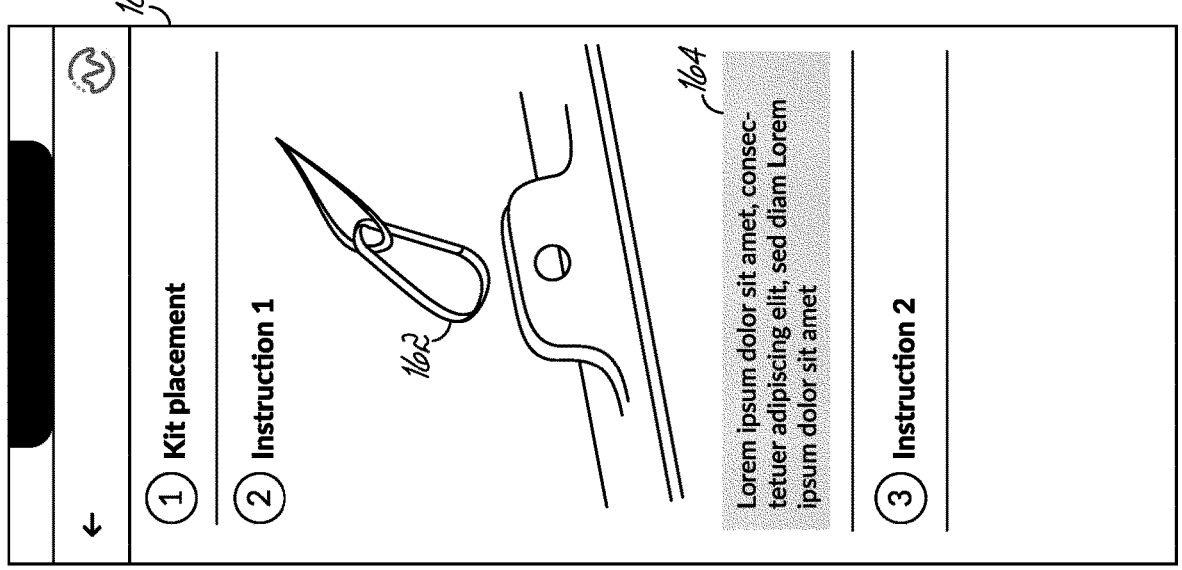

Instruction screens may be sequenced to step the patient 12 through a setup process. For example, as depicted by FIGS. 11 and 12, activating one of the control elements 147-149 may cause the patient device 16 to display a respective instruction screen 150, 160. Each instruction screen 150, 160 may include a graphical element 152, 162 depicting the next step in configuring the exercise device kit (e.g., attaching the door anchor to a door, attaching the other end of the elastic member 28 to the exercise device 14) and a data display field 154, 164 that provides written instructions for the depicted step.

Figure 13:
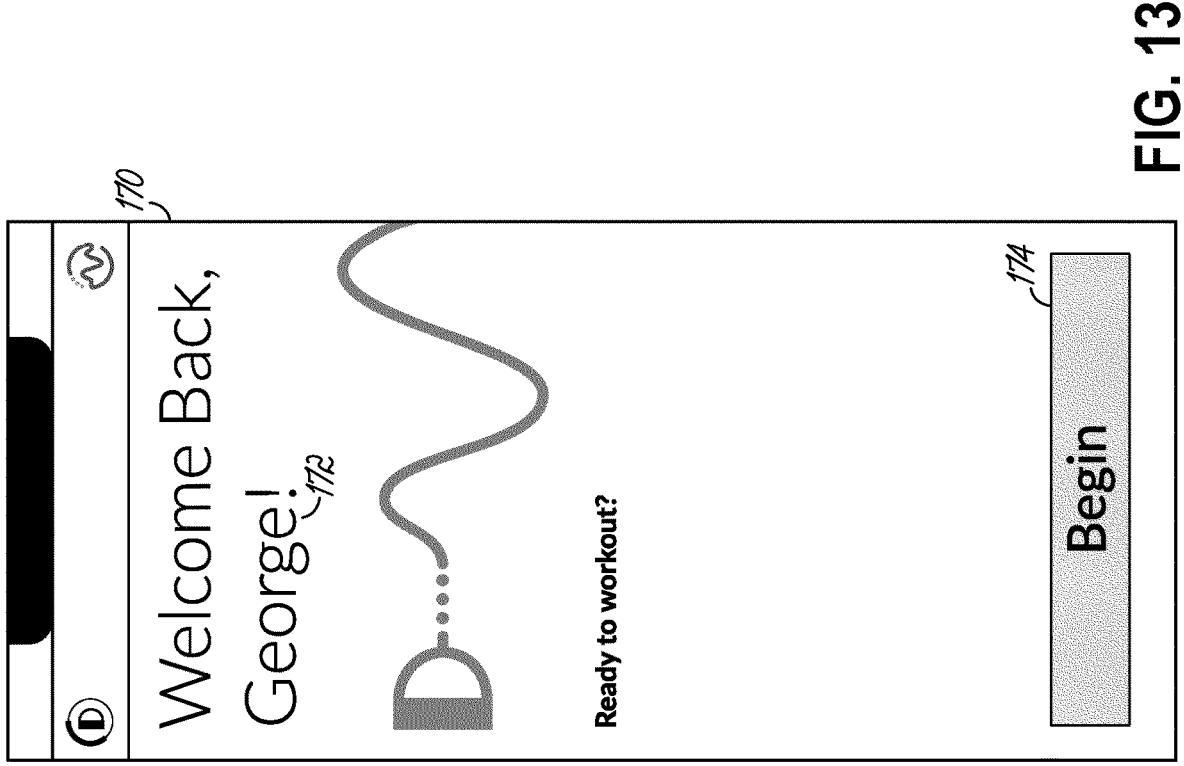
Figure 14:
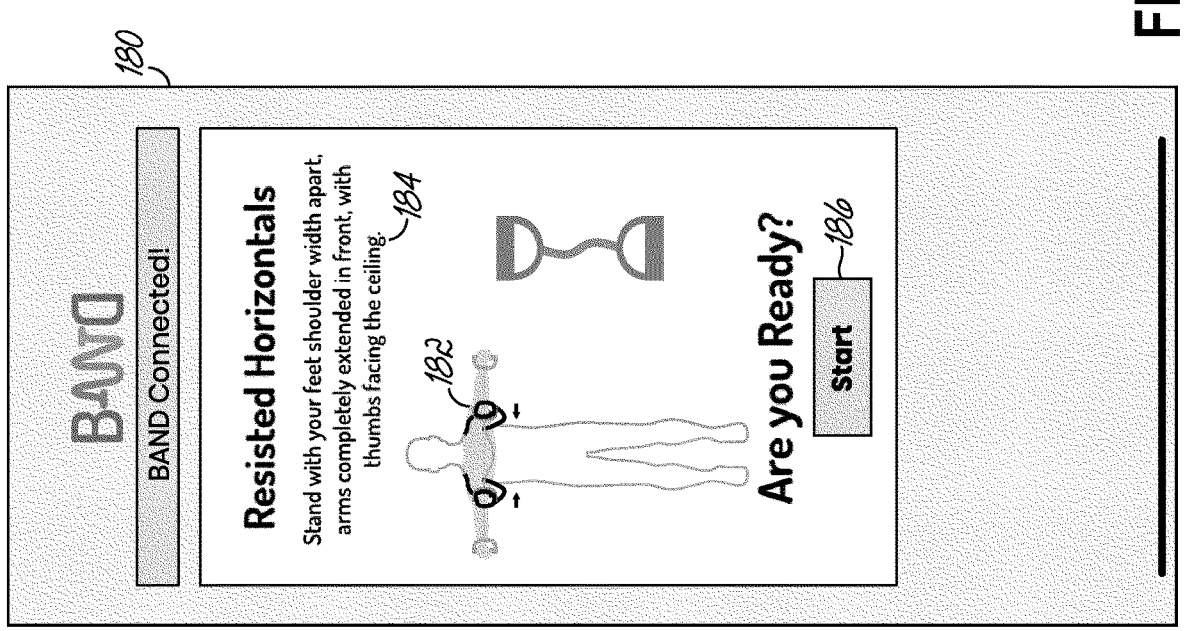

FIG. 13 depicts an exemplary start screen 170 for beginning an exercise session. The start screen 170 may be displayed after the patient 12 has finished a tutorial or, for returning patients, in response to the patient 12 logging in successfully. The start screen 170 may include a graphical element 172 with an appropriate greeting and a control element 174. Activation of the control element 174 may cause the patient device 16 to display a session screen, such as the exemplary exercise instruction screen 180 depicted by FIG. 14.

The exercise instruction screen 180 may include a graphical element 182 that depicts how the exercise in question is to be performed, a data display field 184 with written instructions for performing the exercise, and a control element 186 for starting the exercise session. Information provided by the exercise instruction screen 180 may include directions regarding how to set up for the exercise, such as proper body positioning, equipment placement, and resistance level. The information may also include a position calibration step, such as bringing the exercise devices 14 into contact with each other or the patient device 16, so that a starting position of each exercise device 14 is established at the beginning of the exercise session.

Figure 15:
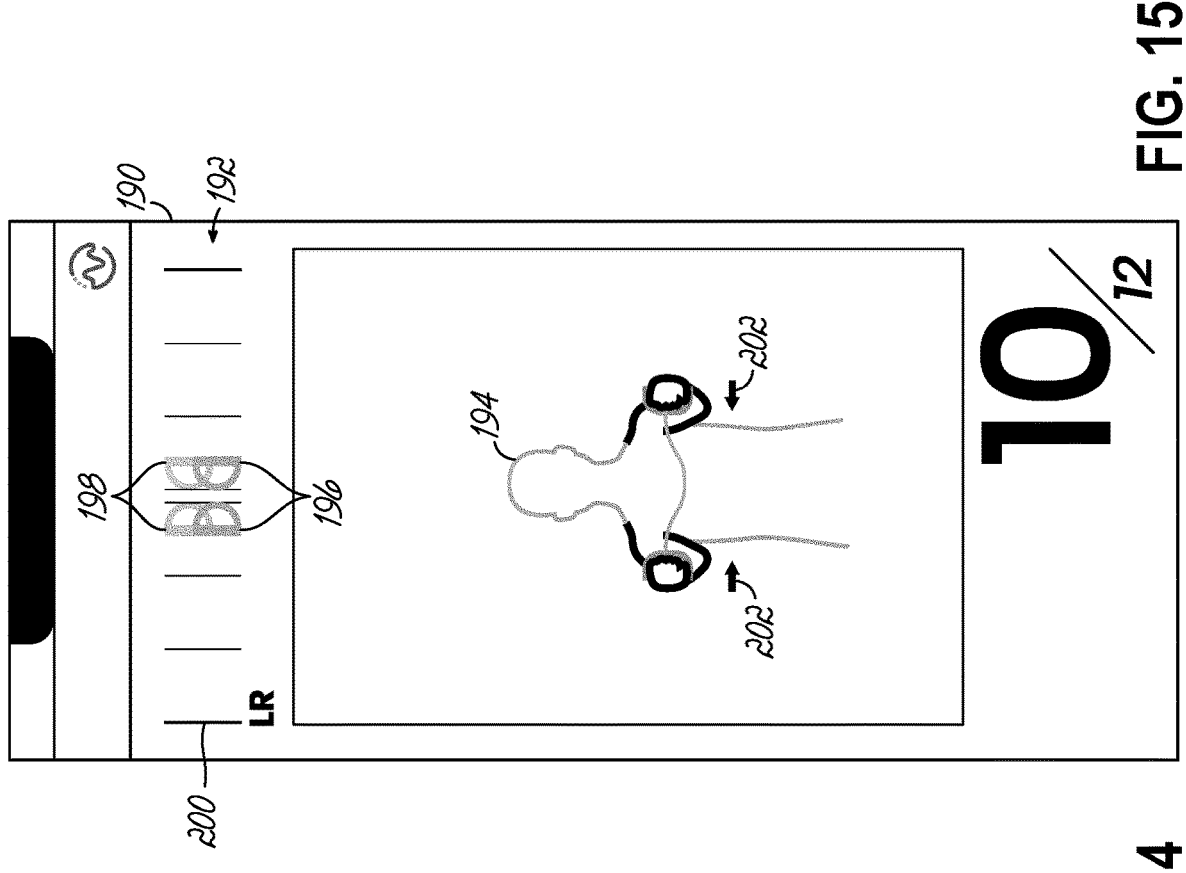

Referring now to FIG. 15, in response to the patient 12 activating the control element 186, the application may cause the patient device 16 to display an action screen 190. The action screen 190 may include a graphical element 192 that depicts a range of motion for the exercise, and another graphical element 194 depicting an animated figure performing the exercise. Animation of the exercise session may be captured using biomechanical models to create an inverse kinematics visual representation of the exercise, using motion capture technology, or using any other suitable method of capturing motion. Embodiments of the present invention may apply game-design elements to provide realistic movement by matching the pose of graphical element 194 to the calibration data and motion data. The graphical element 194 may thereby provide accurate feedback to the patient 12 for each exercise, e.g., in real-time while the exercise is being performed.

The range-of-motion graphical element 192 may include one set of animated handle icons 196 that indicate a current position of the exercise devices 14, another set of animated handle icons 198 that indicate a target position of the exercise devices, and a scale 200 which indicates the relative positions of the handle icons 196, 198 within the range of motion of the exercise. The target position of the exercise device 14 may be based on the patient-specific calibration data described above, and may depict movement in accordance with what was recorded by the therapist during a previous in-person session. Thus, the target positions of the exercise device 14 displayed by the application may reflect a form, pace, range of motion, and exertion level for the exercise session which is personalized to the patient 12. A vertical line in the center of the range-of-motion graphical element 192 may indicate a starting position, and the left/right vertical lines may indicate a calibrated range of motion for the exercise set. A line connecting the animated handle icons 196 may have a color indicating the type of elastic member 28 to be used for the exercise session. For ease of use, the color displayed by the patient application may match the color of an elastic member 28 provided in the exercise device kit.

The action screen 190 may initially provide the patient 12 with information indicating a starting position for the exercise session. Arrow icons 202 proximate to the animated figure may then provide the patient 12 with an indication of which direction the exercise devices 14 should be moved. The action screen 190 may thereby provide the patient 12 with real-time indications of how the exercise is to be performed, as well as feedback on how closely their movements are tracking the target positions and a count of the number of repetitions performed. While the exercise session is in progress, the application may store data that establishes a record of the exercise session, e.g., time, date, location, user, and motion data. This data may be stored locally in the patient device 16, uploaded to the database 22, or both stored locally and in the database 22.

Figure 16:
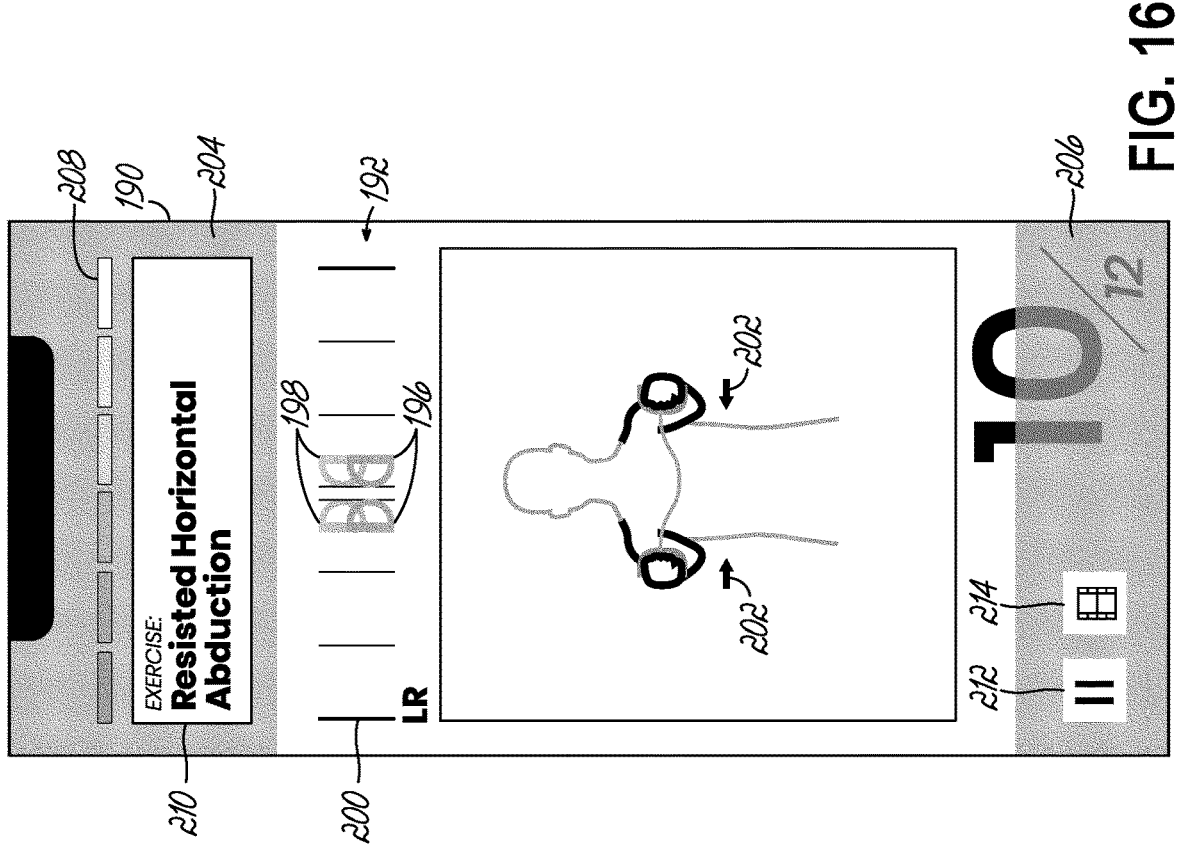

FIG. 16 depicts the action screen 190 as it may appear in response to input from the patient 12, e.g., in response to the patient 12 touching the display of the patient device 16. In response to this input, the action screen 190 may further display one or more of a drop-down graphical element 204 and a pop-up graphical element 206. The drop-down graphical element 204 may include a session progress bar 208 that provides an indication of how far the patient 12 has progressed into the exercise session, and a data display field 210 that provides information about the exercise, e.g., the name or type of exercise being performed. The pop-up graphical element 206 may include one or more icons, such as a pause/start icon 212 and a film icon 214. Activating the pause/start icon 212 may cause the application to alternatively pause/start the exercise session. Activating the film icon 214 may cause the application to replay all or a portion of the exercise session which has been recorded, or play an animation showing how to perform the exercise.

Figure 17:
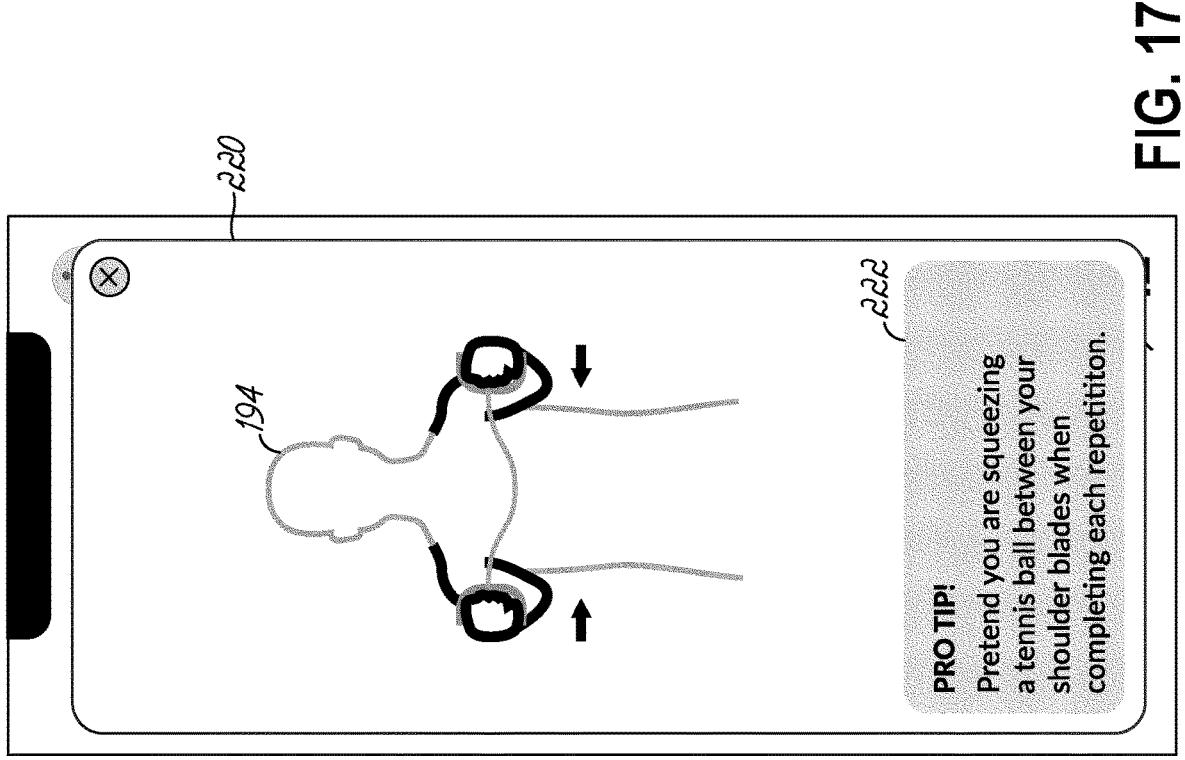

FIG. 17 depicts a pop-up window 220 that may be displayed on the patient device 16 in response to the patient 12 activating the film icon 214. The pop-up window 220 may provide information to the patient 12 in the form of the animated figure icon 194 performing the exercise, and a data display field 222 including information regarding how to perform the exercise.

Figure 18:
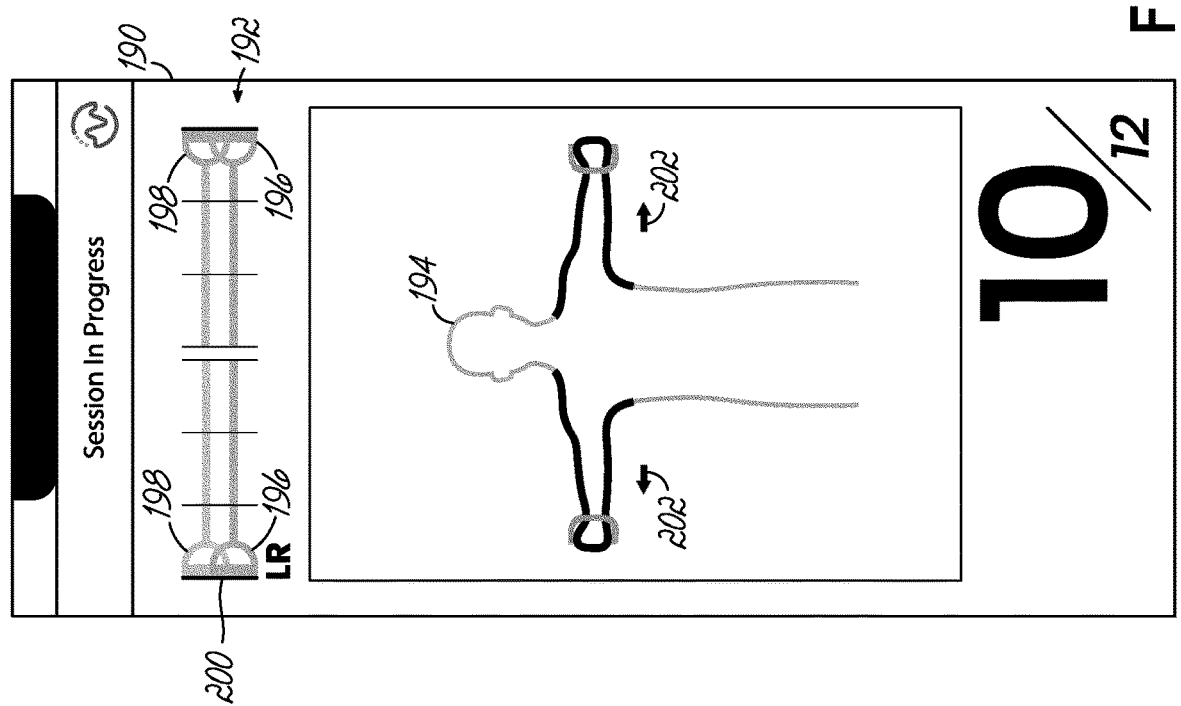

Referring now to FIG. 18, during the exercise session, at least a portion of each of the range-of-motion graphical element 192 and animated figure graphical element 194 may move in concert with the current motion of the exercise devices 14, while other portions may move in concert with the target motion (i.e., the target position verses time) of the exercise devices 14. The current motion of the exercise devices 14 may be determined based on data received from the sensor module 62. The target motion of the exercise devices 14 may be determined based on the calibration data. In response to the current motion matching the target motion, the range-of-motion and animated figure graphical elements 192, 194 may provide feedback indicating that the patient 12 is performing the exercise properly. This feedback may be in the form of a color of the graphical elements, e.g., a green color. Whether or not the current motion matches the target motion may be determined, for example, by comparing a sum of the squares of the distance between the current motion and the target motion to a predetermined threshold. If the current motion is within the predetermined threshold of the target motion, the current motion may be considered as matching the target motion.

Figure 19:
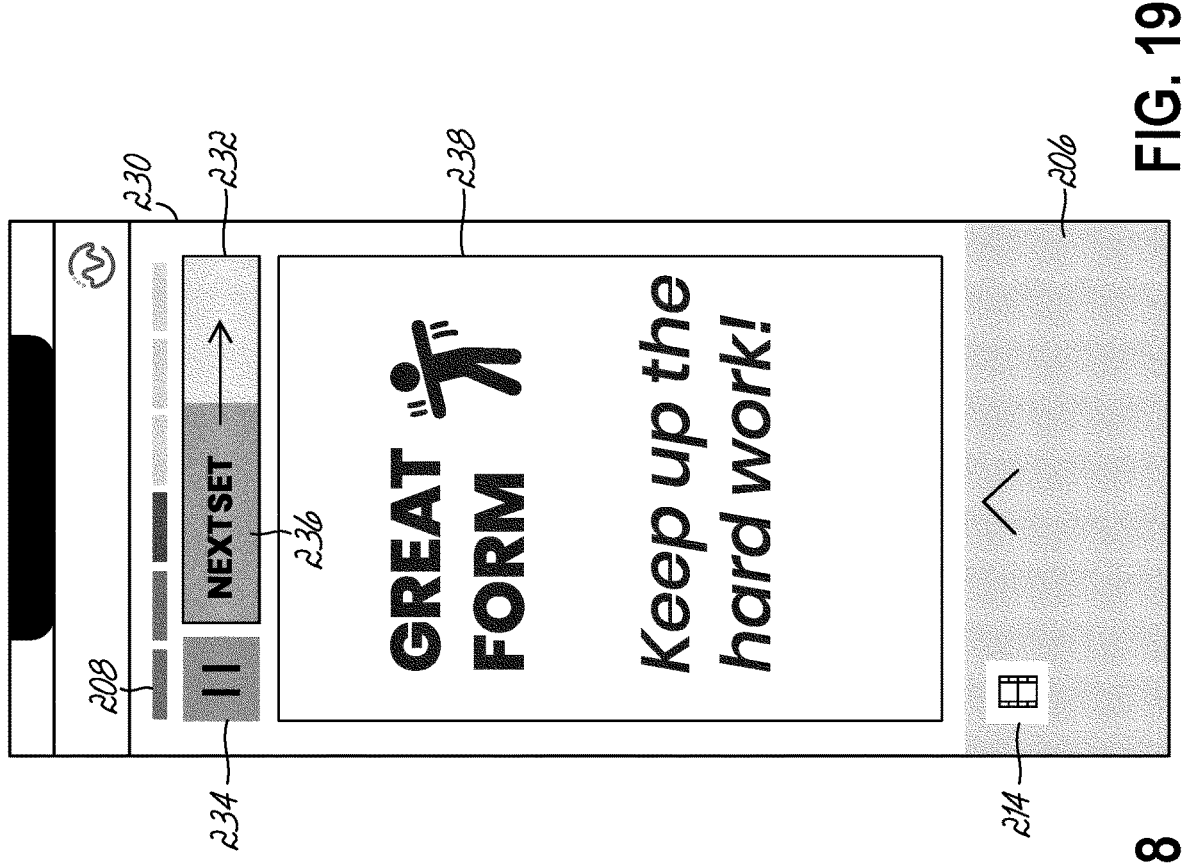

As shown by FIG. 19, in response to the patient 12 finishing an exercise set during which the patient 12 maintained good form, the application may cause the patient device 16 to display a between set screen 230. The between set screen 230 may include the pop-up graphical element 206, film icon 214, session progress bar 208, a graphical element 232 including a pause/start icon 234 and a slider icon 236 that enables the patient 12 to start the next set of the exercise session, and a graphical element 238 that encourages the patient 12 to maintain good form. In an embodiment of the present invention, the application may prohibit the patient 12 from starting the next session until a predetermined amount of time has passed. This rest time between sessions may be set by the physical therapist, e.g., during a calibration session with the patient 12.

Figure 20:
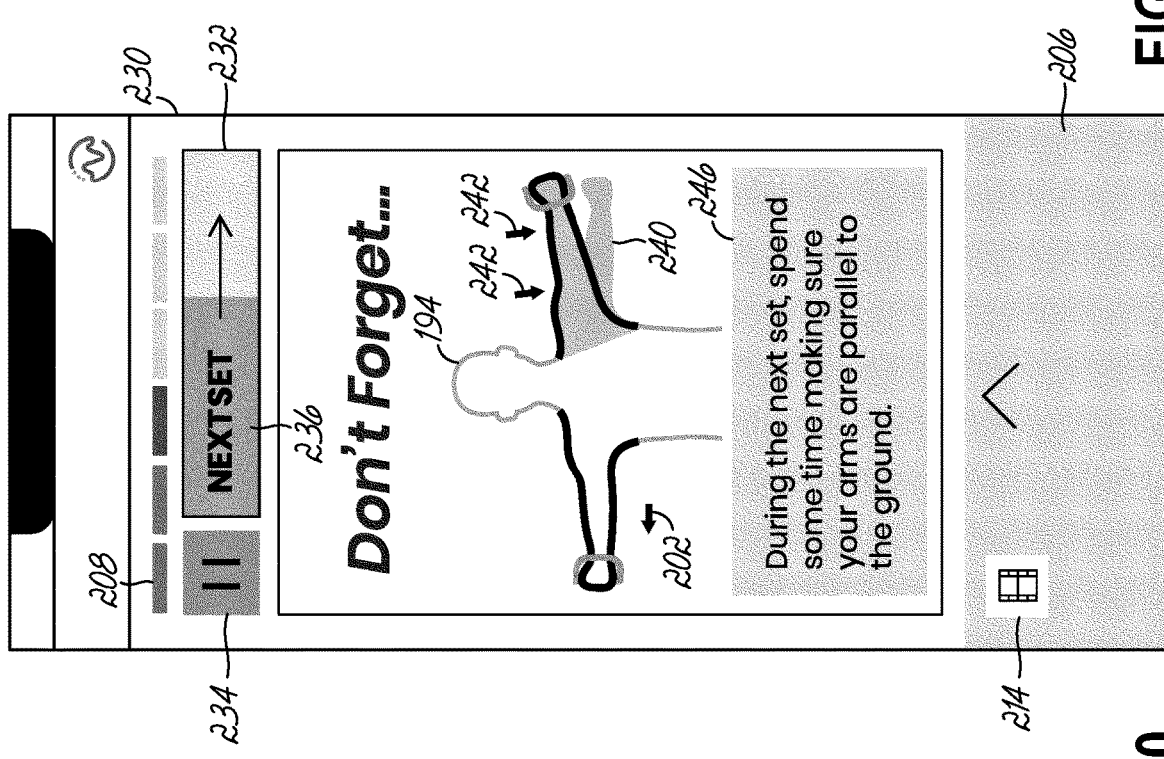
Figure 21:
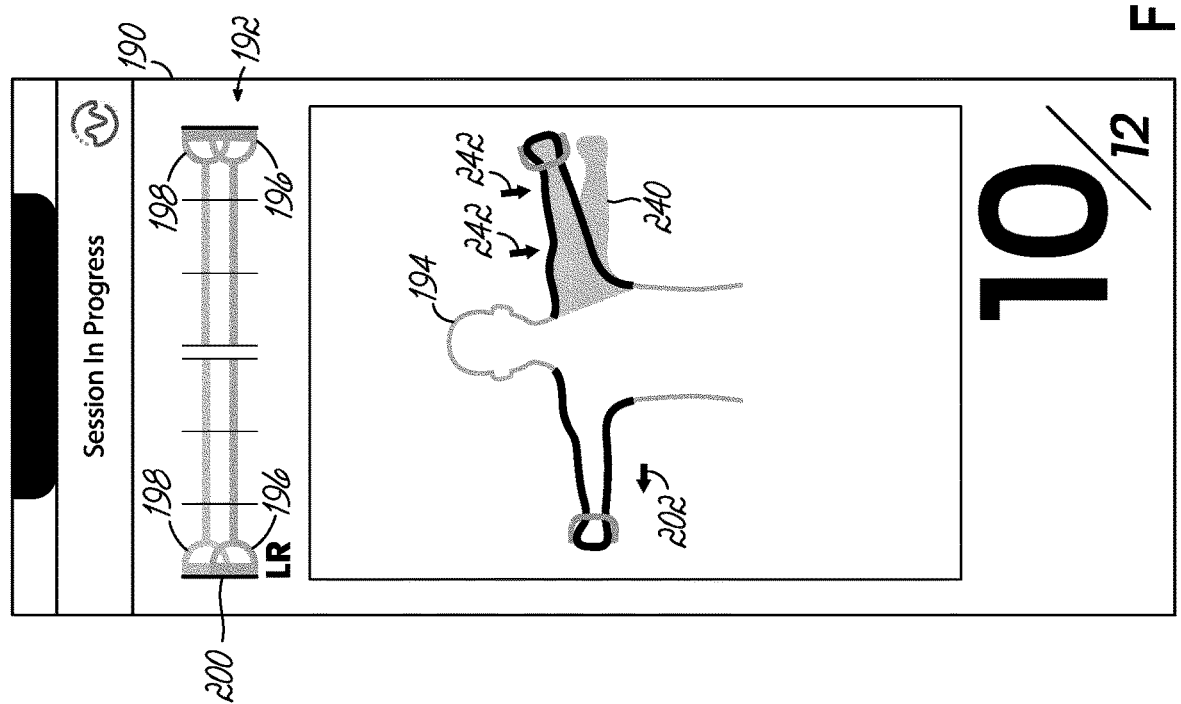

Referring now to FIG. 20, in response to the current motion of the exercise devices 14 not matching the target motion, the range-of-motion and animated figure graphical elements 192, 194 may provide feedback indicating that the patient 12 is performing the exercise improperly. This feedback may be provided by one or more of the color and position of the graphical elements, e.g., an arm 240 of the animated figure graphical element 194 turning red and being raised. Additional graphical elements (e.g., arrows 242) may provide an indication of how to correct the movement. In response to the patient 12 finishing an exercise set during which the patient 12 did not maintain good form, the application may cause the patient device 16 to display a between set screen such as the exemplary between set screen 230 of FIG. 21. The between set screen 230 includes a graphical element 194 and a data display field 246 which reminds the patient 12 of how to correct their form during the next exercise set.

Figure 22:
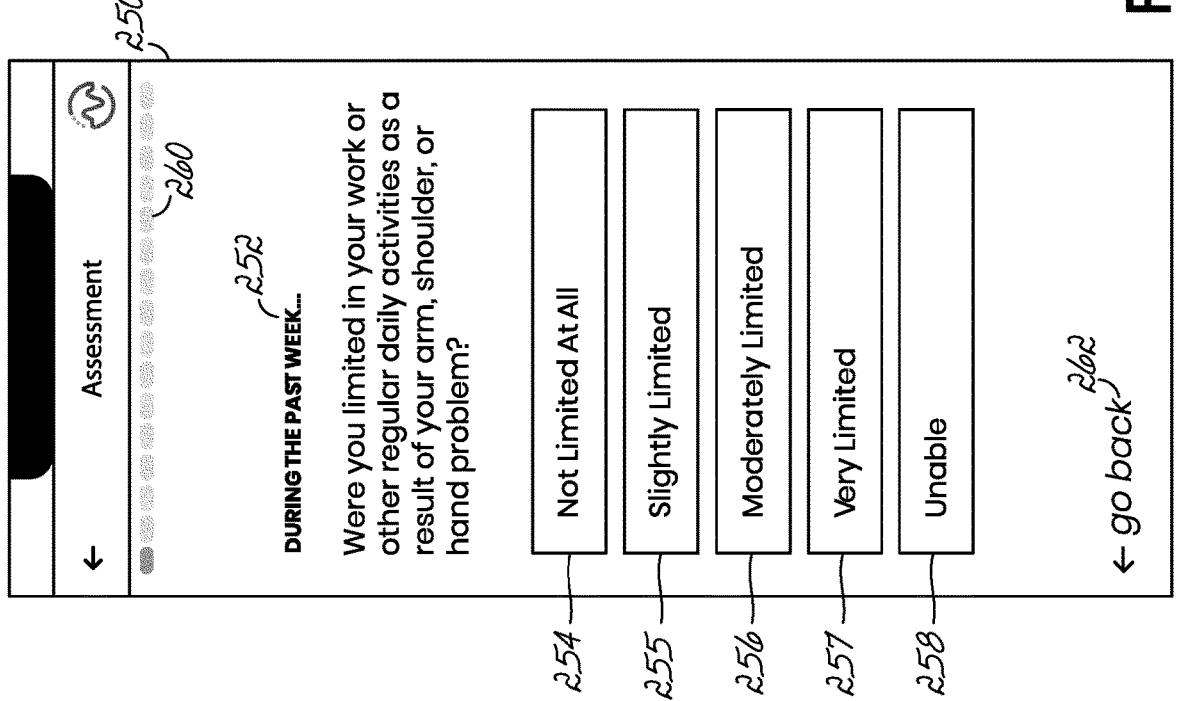

FIG. 22 depicts an exemplary assessment screen 250 which may be displayed by the patient device 16 after the exercise session has been completed. The assessment screen 250 may include a data display field 252 that presents a question to the patient 12, and a plurality of control elements 254-258 which the patient 12 can activate in order to answer the question. The assessment screen 250 may be one of a plurality of assessment screens, each of which asks the patient 12 a different multiple choice question. An assessment progress bar 260 at the top of the assessment screen 250 may provide the patient 12 with an indication of how far they have progressed through the assessment process. A navigation icon 262 at the bottom of the assessment screen 250 may enable the patient 12 to return to a previous screen, or advance to a subsequent screen. Advantageously, this feature may enable the use of patient reported outcomes without the need to provide access to clinician in real time, or require an office visit by the patient 12.

Figure 23:
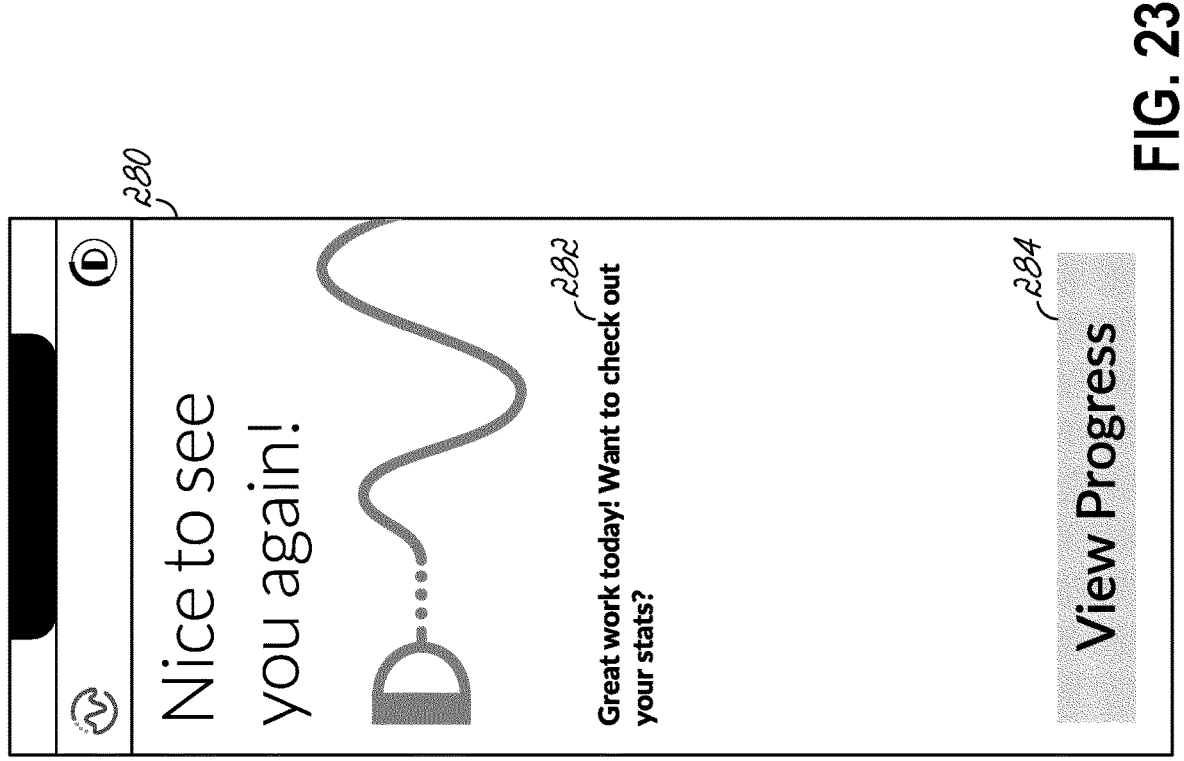
Figure 24:
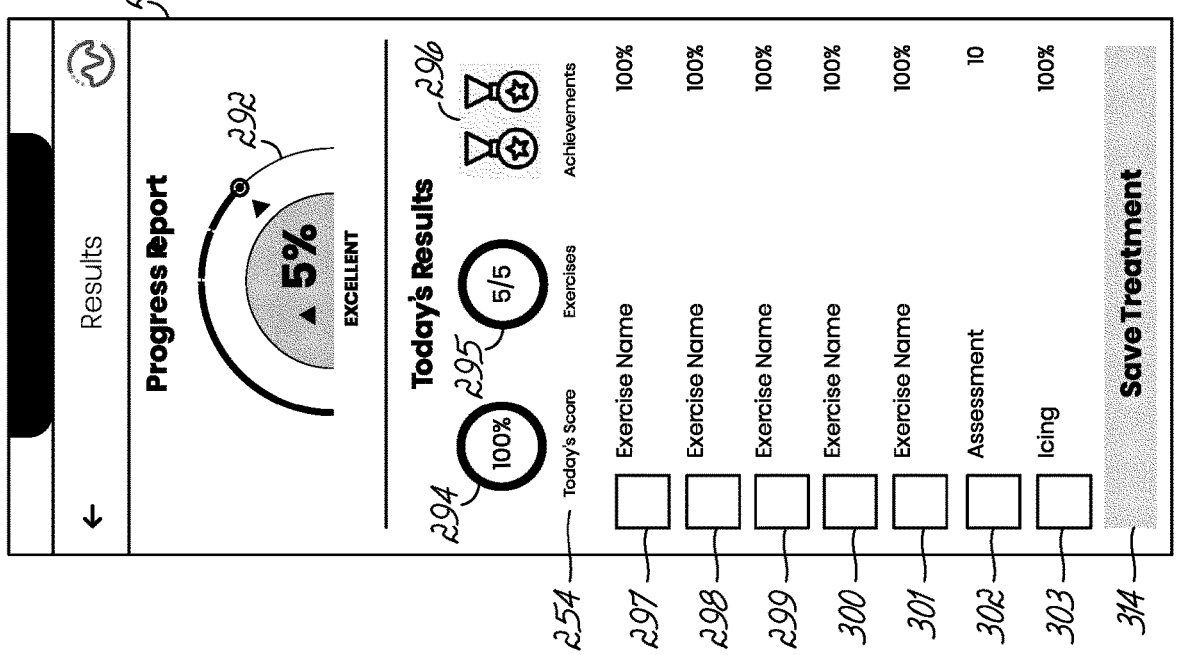

FIG. 23 depicts an exemplary sign-off screen 280 which may be displayed by the patient device 16 in response to the patient 12 completing the assessment portion of the exercise session. The sign-off screen 280 may include a graphical element 282 asking the patient 12 if they would like to view their progress, and a control element 284. In response to the patient 12 activating the control element 284, the patient device 16 may display a progress report screen, such as the exemplary progress report screen 290 depicted by FIG. 24. The progress report screen 290 may include a graphic element 292 that provides an indication of the patient's performance relative to previous exercise sessions, graphic elements 294-303 that provide feedback on the patient's performance for the most recent exercise session, and a control element 314 activation of which causes the application to save the session data.

Figure 25:
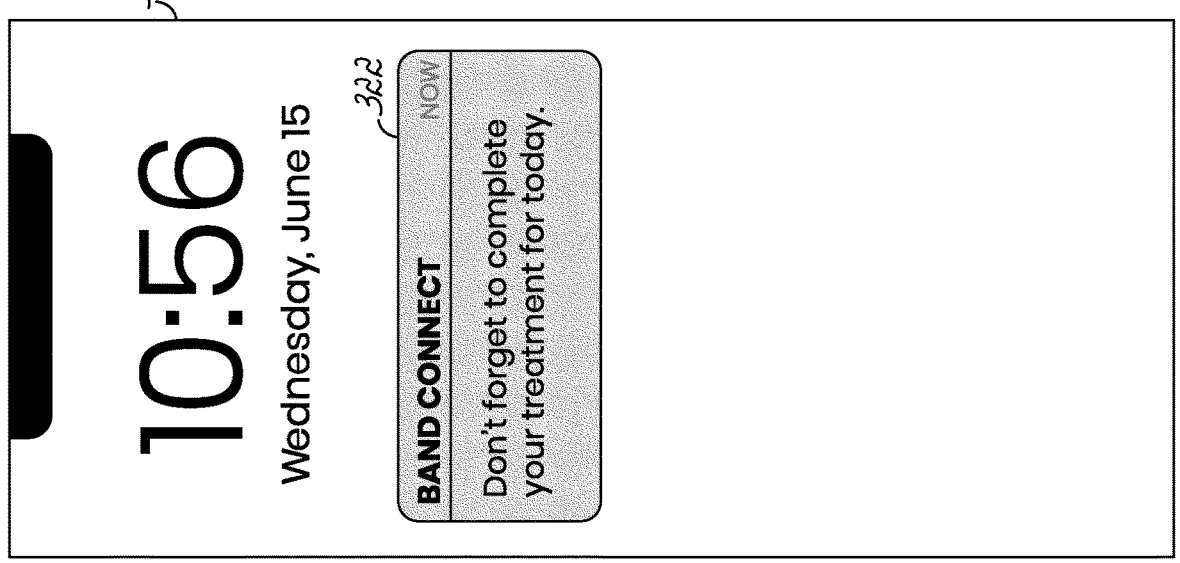

Referring now to FIG. 25, the application may occasionally cause the patient device 16 to display a reminder screen 320 that includes a data display field 322. The data display field 322 may provide the patient 12 with information regarding an exercise session, such as a date and time for which the exercise session is scheduled. The reminder screen 320 may be displayed, for example, if the patient 12 has not completed an exercise session by a certain time on a day the exercise session has been scheduled.

Figure 26:
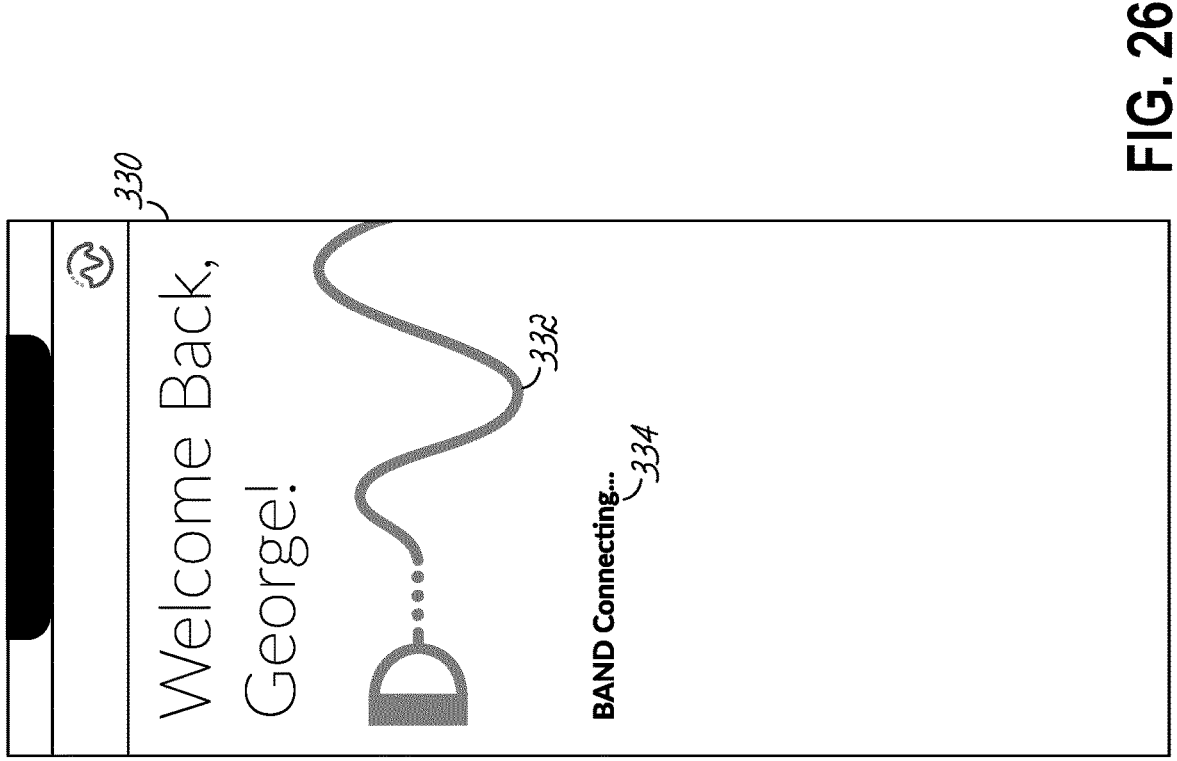

FIG. 26 depicts a connection screen 330 that may be displayed by the patient device 16 in response to a patient 12 who has previously logged into the rehabilitation platform initiating an exercise session. The connection screen 330 may include a graphical element 332 which displays an appropriate greeting (e.g., "Welcome back, George!"), and a graphical element 334 that provides an indication of a status of the connection between the exercise devices 14 and patient device 16.

Figure 27:
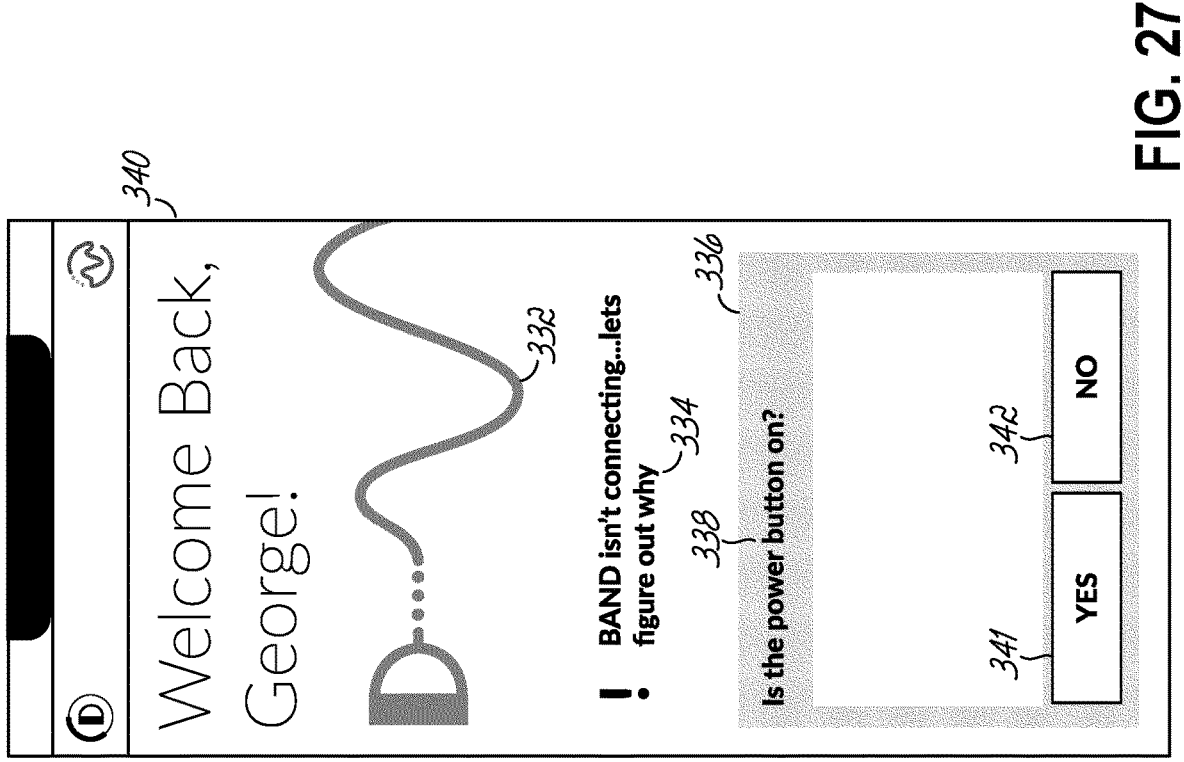

In some cases, the patient device 16 may be unable to connect to one or more of the exercise devices 14. In this case, the application may cause the patient device 16 to display a trouble shooting screen, such as the exemplary trouble shooting screen 340 depicted by FIG. 27. The trouble shooting screen 340 may include the graphical element 332, a graphic element 334 that describes the problem encountered, and a graphical element 336 which guides the patient 12 through a trouble shooting process. The process graphical element 336 may include a data display field 338 that asks the patient 12 a question, and one or more control elements 341-342 that enable the patient 12 to answer the question. The trouble shooting process may display a plurality of trouble shooting screens in a sequence that depends on the answers entered by the patient 12.

Therapist Application

The therapist application may facilitate goal setting and goal tracking. Goal metrics may include pain levels, function, range of motion, and strength. Goals may be set by the therapist based on outcome and progress predictions, which in turn may be based on trends. To create an exercise session, the therapist may login to the therapist application (e.g., through the therapist device 18), and select a patient from a list of patients representing patients in the database 22. The therapist may then activate a "build treatment" feature, and proceed to select one or more exercises from a library of exercises. The therapist may then define a number of sets of the exercise in the exercise session, a number of repetitions of the exercise in each set, and the resistance band level needed to complete the exercise. To calibrate the exercises, the therapist may first demonstrate the exercise to the patient 12. The therapist may then have the patient 12 perform the exercise using one or more exercise devices 14 (depending on the type of exercise) while the system records the motion data received from the exercise device 14. When the therapist is satisfied with the patient's movement, they may activate a calibration feature to identify the data being collected as "calibration data". The therapist may repeat the calibration procedure with each type of exercise prescribed to the patient 12. The calibration data may then be stored in the database 22.

Figure 28:
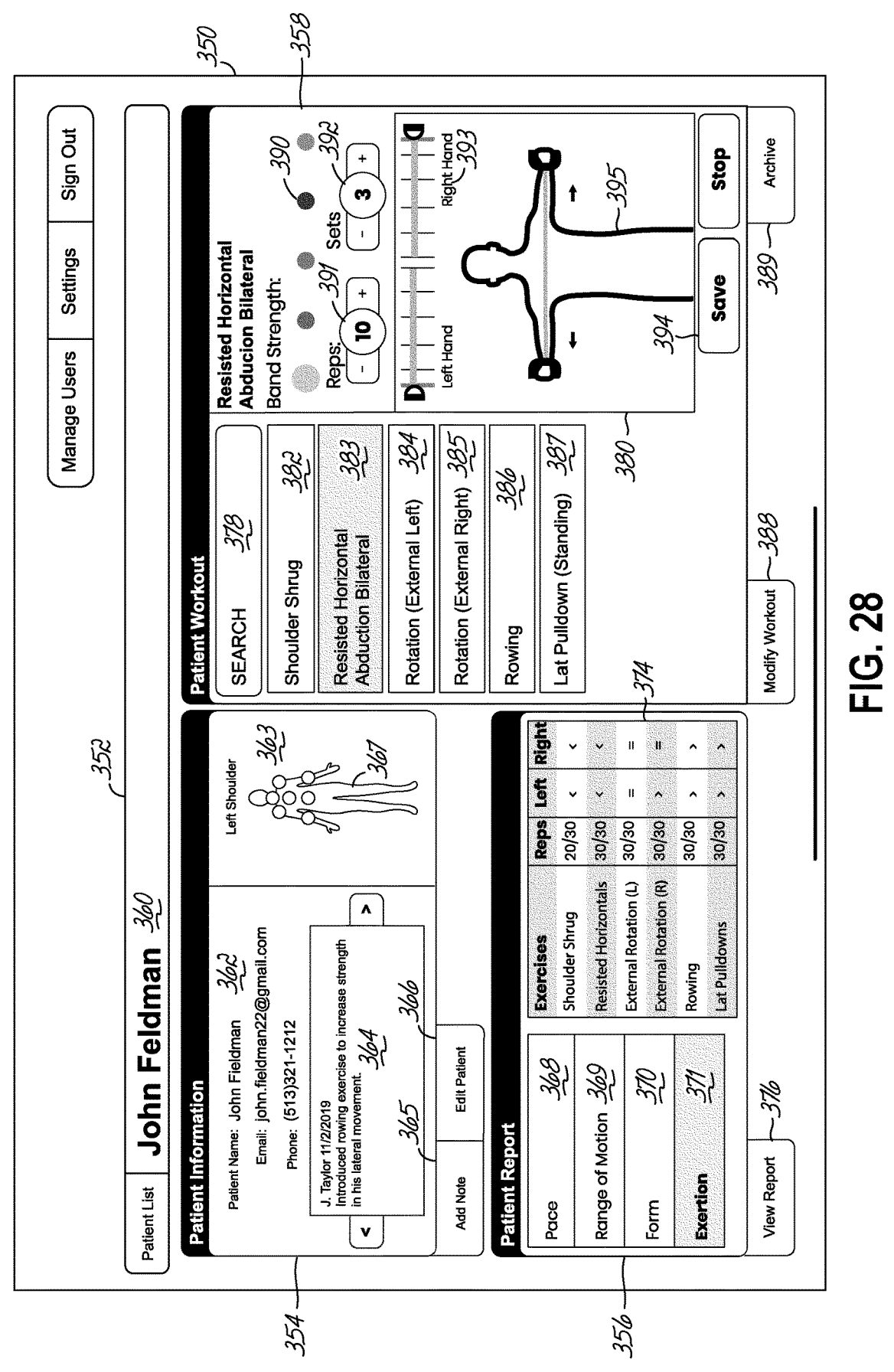

FIG. 28 depicts a patient data home screen 350 that may be displayed by the therapist application. The home screen 350 may include a patient list window 352, a patient information window 354, a patient report window 356, and a patent treatment window 358. The patient list window 352 may include a data entry field 360 into which the therapist can enter a patient identifier, e.g., the patient's name. In response to the patient identifier being entered into the data entry field 360 of patient list window 352, the therapist device 18 may transmit a query to the server 20 for data relating to the patient 12. In response to receiving the query from the therapist device 18, the server 20 may transmit a database query to the database 22 requesting data that conforms to the query received from the therapist device 18. In response to receiving the search results from the database 22, the server 20 may transmit a reply to the therapist device 18 including the requested data. This data may be stored in a local memory and used to populate various windows that are displayed by the therapist application.

The patient information window 354 may include one or more data display and entry fields 362-364, an add note tab 365, and an edit patient tab 366. The data display fields 362, 363 may display text and graphical data, such as the patient's name, contact information, and a graphical element 367 indicating areas of the patient's anatomy which are being treated. The data entry field 364 may allow the therapist to enter notes regarding interactions with the patient 12, the results of the patient's exercise sessions, or data for creating a new patient file.

The patient report window 356 may include a plurality of control elements 368-371 for selecting a patient performance metric, such as a "Pace" button, a "Range of Motion" button, a "Form" button, and an "Exertion" button. The patient report window 356 may also include an exercise window 374 that displays a list of exercises that can be or have been prescribed to the patient 12, and a "view report" tab 376. Activation of view report tab 376 may cause the therapist device 18 to display a patient report screen for the selected metric.

The patient treatment window 358 may include a data entry field 378 for entering search terms, an exercise session design window 380, a plurality of control elements 382-387 for selecting an exercise, and a modify treatment tab 388. The exercise session design window 380 may include a band strength selection window 390, a repetition control element 391, a set control element 392, and a range adjustment control element 393. The therapist may design an exercise session by first selecting the type of exercise using the exercise control elements 382-387. The therapist may then set the number of repetitions and number of sets for the exercise session using the repetition and set control elements 391, 392. Once the therapist is satisfied with the exercise session, the session can be saved to the patient's file by activating a save control element 394.

The patient treatment window 358 may also include a graphical element 395 (e.g., an animated figure) that shows the patient's range of motion and pace during a therapy session. The pose of the animated figure may be based on data received by the therapist device 18 from the exercise devices 14 during the therapy session. The therapist may use the range of motion measured for the patient 12 during the therapy session to help design one or more exercise sessions to be performed by the patient 12 outside the office. For example, the therapist may record the patient's movement, and use the recorded movement as a basis for designing an exercise session. To this end, the recorded movement may be used as is or modified by the therapist to provide the calibration data.

Figure 29:
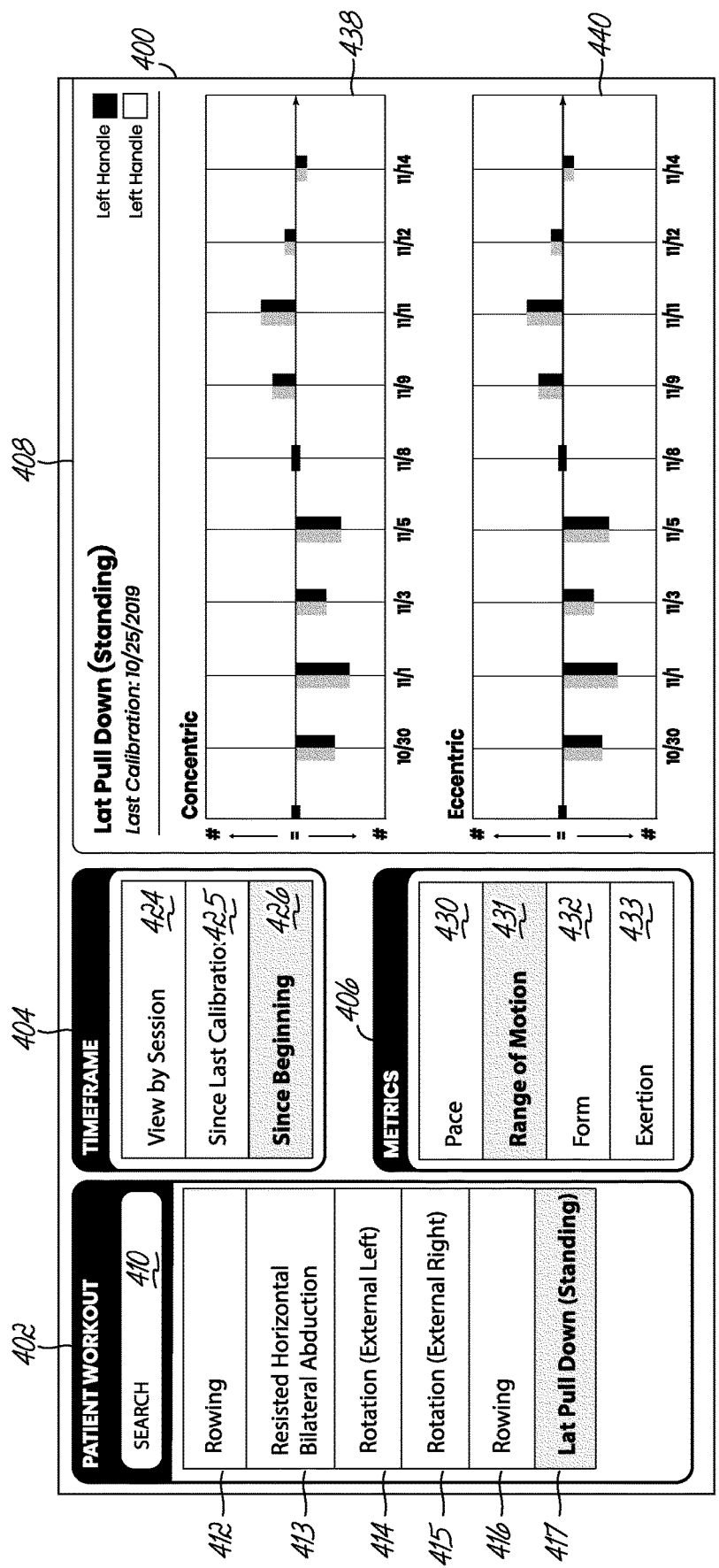
Figure 30:
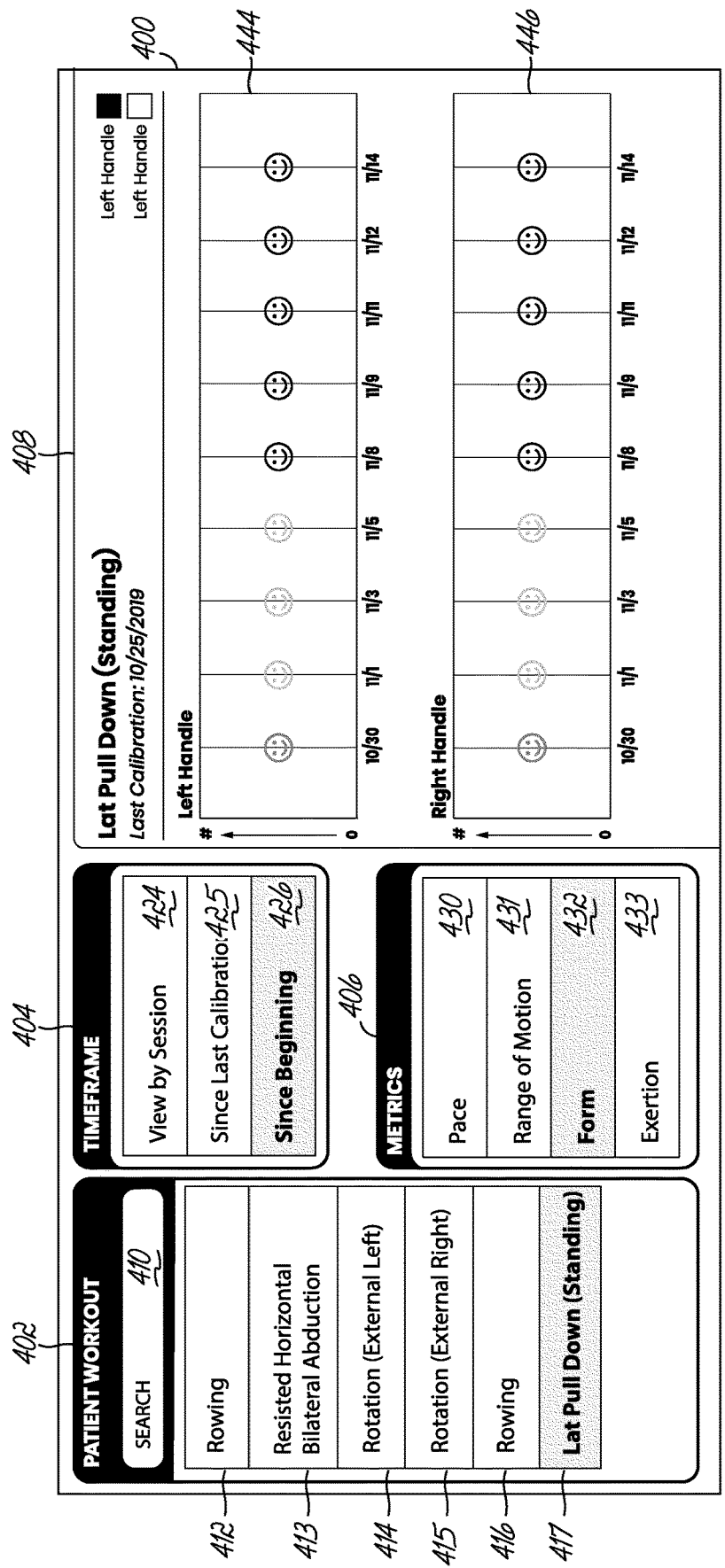

FIG. 29 depicts an exemplary patient report screen 400 that may be displayed by the therapist device 18 in response to the therapist activating the view report tab 376 of patient report window 356. The patient report screen 400 may include a patient treatment selection window 402, a timeframe selection window 404, a metrics selection window 406, and a results display window 408. The patient treatment selection window 402 may include a data entry field 410 for entering search terms, and one or more control elements 412-417 for selecting an exercise, e.g., "Rowing", "Resisted (Horizontal Abduction Bilateral)", "Rotation (External Left)", "Rotation (External Right)", or "Lat Pull Down—Standing".

The timeframe selection window 404 may include a plurality of timeframe selection control elements 424-426, such as a "View by Session" button, a "Since Last Calibration" button, and a "From Beginning" button. The metrics selection window 406 may include a plurality of metric selection control elements 430-433, such as a "Pace" button, a "Range of Motion" button, a "Form" button, and an "Exertion" button.

In response to activation of a combination of exercise, timeframe, and metric control elements, the therapist application may select relevant portions of the data downloaded from the database 22 (or launch a query to the database 22 to retrieve the relevant data) to populate the results display window 408. The results display window 408 may include a plurality of graphical elements 438, 440 that display data in a form which is easily readable. For example, each of the graphical elements 438, 440 may include a bar graph that illustrates results for each exercise session for each of a plurality of time periods. By providing the therapist with detailed metrics describing the patient's experience and progress over time, the patient report screen 400 may provide the therapist with insights from condition-specific assessments completed by the patient 12 periodically through their treatment. These insights may include whether the patient 12 is adhering to the prescribed treatment, is using the correct technique, and how well the patient's recovery is progressing.

Figure 31:
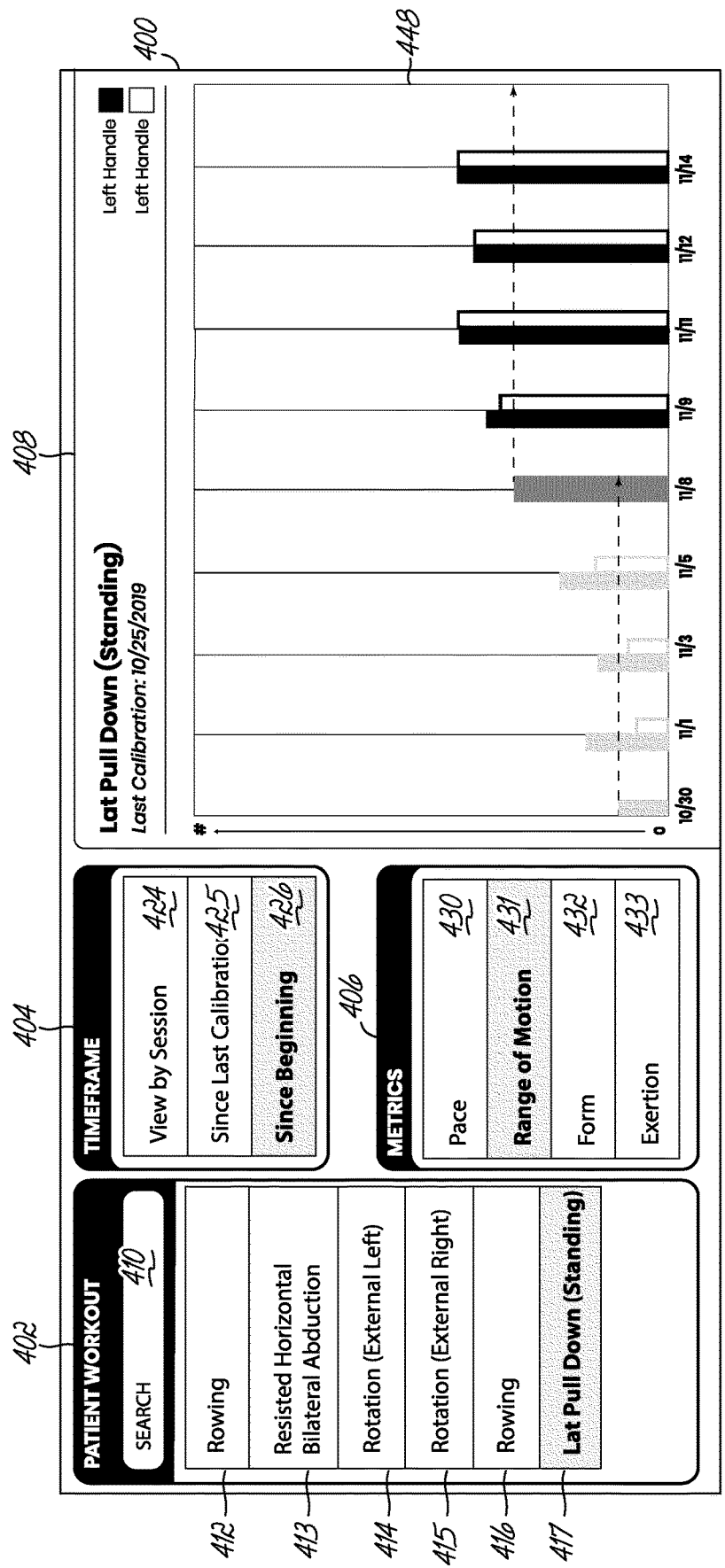
Figure 32:
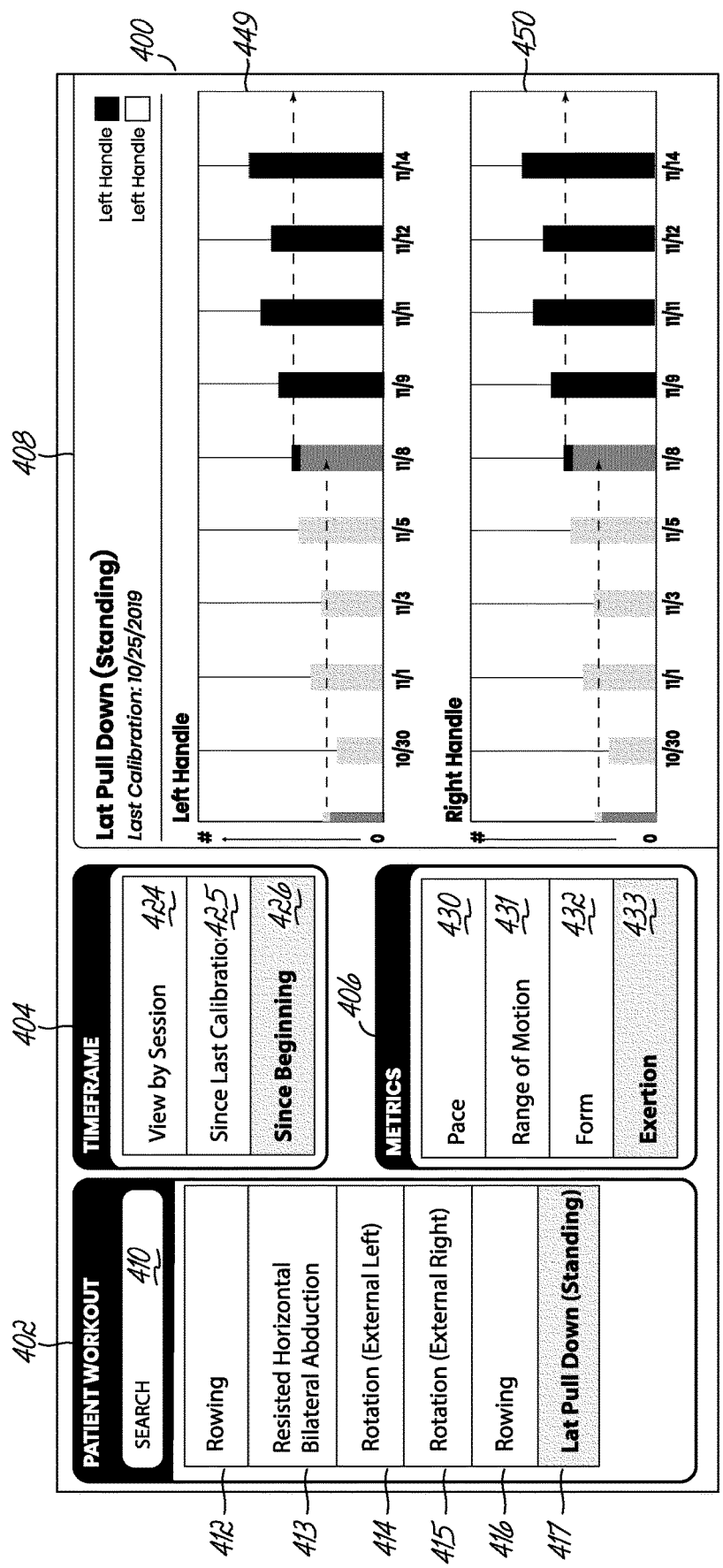

Activating a different control element in one or more of the patient treatment, timeframe, or metrics selection windows 402, 404, 406 may cause the host computer to update the results display window. For example, as depicted by FIG. 32, activating the "Exertion" button (thereby deactivating the "Pace" button shown as activated in FIG. 29) may cause the results display window 408 to display graphical elements 444, 446 that provide information relating to the form of the patient 12 while performing Lat Pull Down exercises for the selected timeframe. FIGS. 31 and 32 likewise depict the results display window 408 with graphical elements 448-450 corresponding to activation of the "Range of Motion" and "Exertion" buttons, respectively, of metrics window 406.

Figure 33:

FIG. 33 depicts an exemplary patient report screen 452 that provides a graphical view of the patient's range of motion. As part of the treatment protocol, the therapist application may enable clinicians and physical therapists to measure and store various measurements in the database 22. Over time, clinicians can review the progress a patient is making, and determine how well the patient is improving as compared to an expected recovery rate. The patient report screen may include a graphical element depicting an active range of motion measurement. The user interface may allow the clinician to input where on this range motion the patient fits during each clinic visit.

FIG. 34 depicts an exemplary patient report screen 454 that provides a graphical view of a patient outcome report. A physical therapist may assign the assessments they would like the patient to complete while they are creating or modifying the patient's treatment using the therapist device 18. Once the patient has completed the assessment using the patient application, the captured information may be displayed in the patient report section of the therapist application. These assessments may be used to determine how a patient is doing relative to their goals and expected progress.

Figure 35:
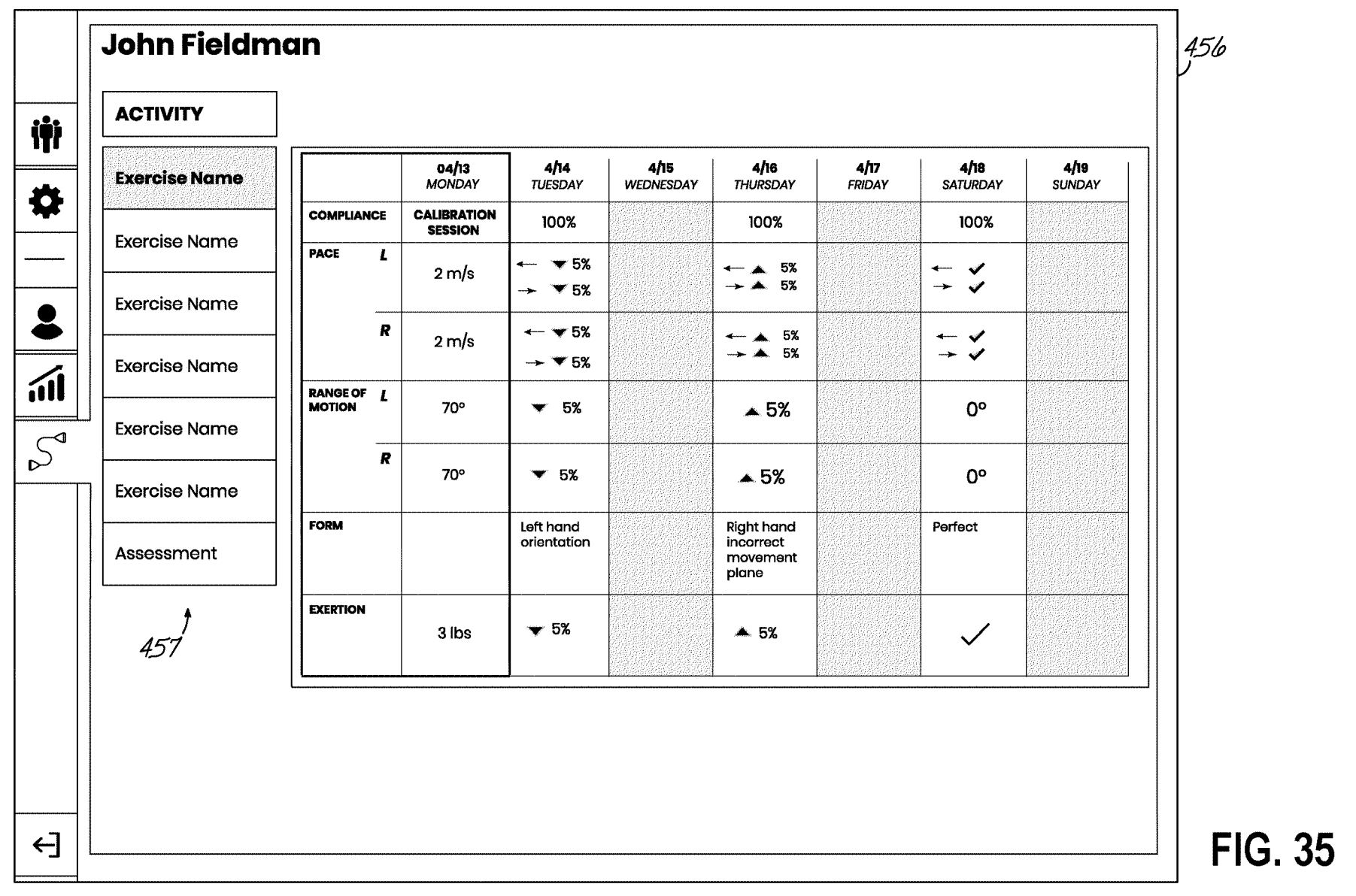

FIG. 35 depicts another exemplary patient report screen 456 that provides a graphical view of a patient's progress. Layout and timeframe of the patient report screen 456 may be changed to accommodate in-clinic measurements and assessment updates. Both in-clinic measurements and assessments may be displayed in an activity column 457. The activity column may be configured so that the clinician can sort activities performed since last calibration, by session, or since the beginning of treatment.

Figure 36:
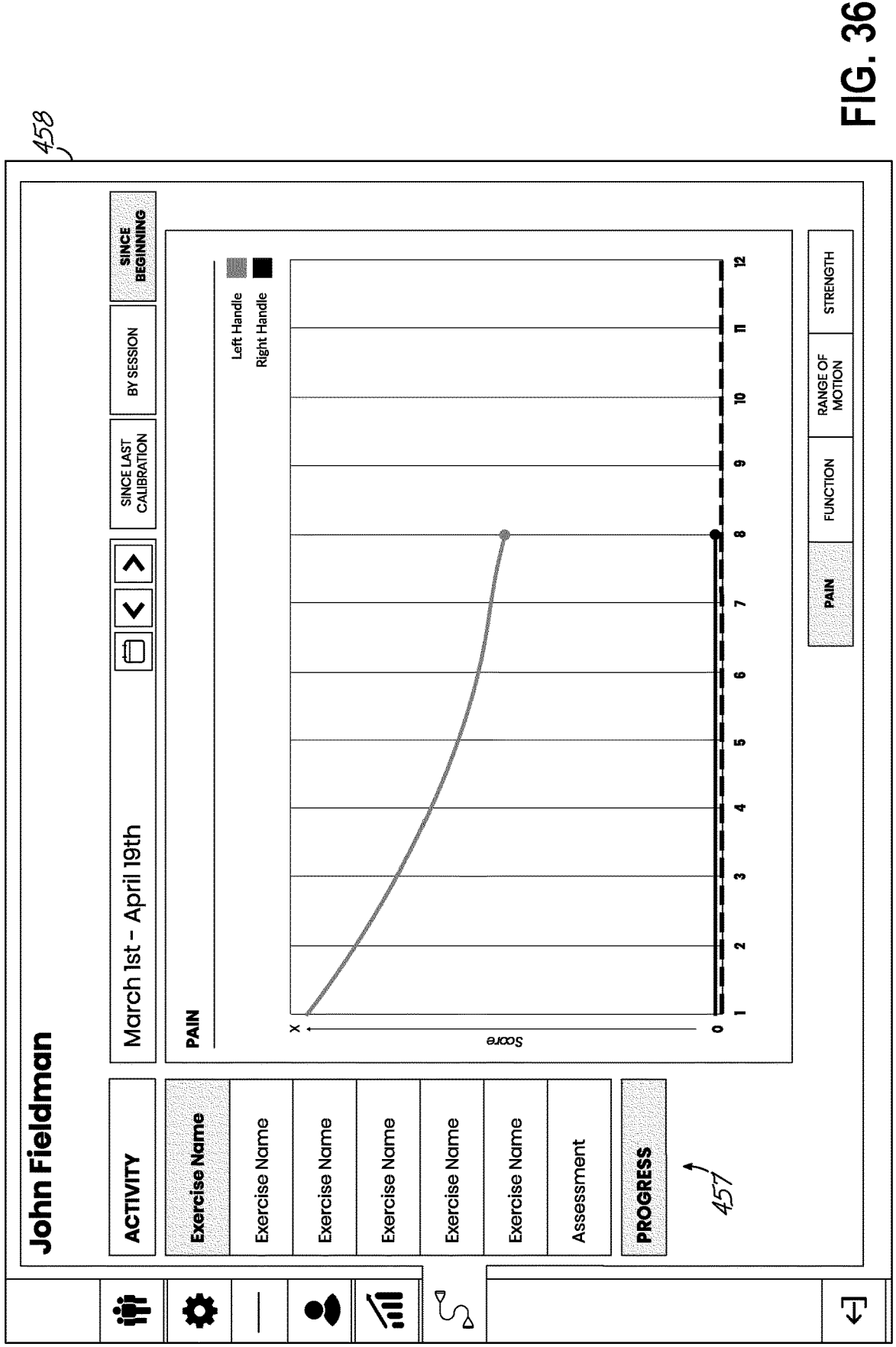
Figure 37:
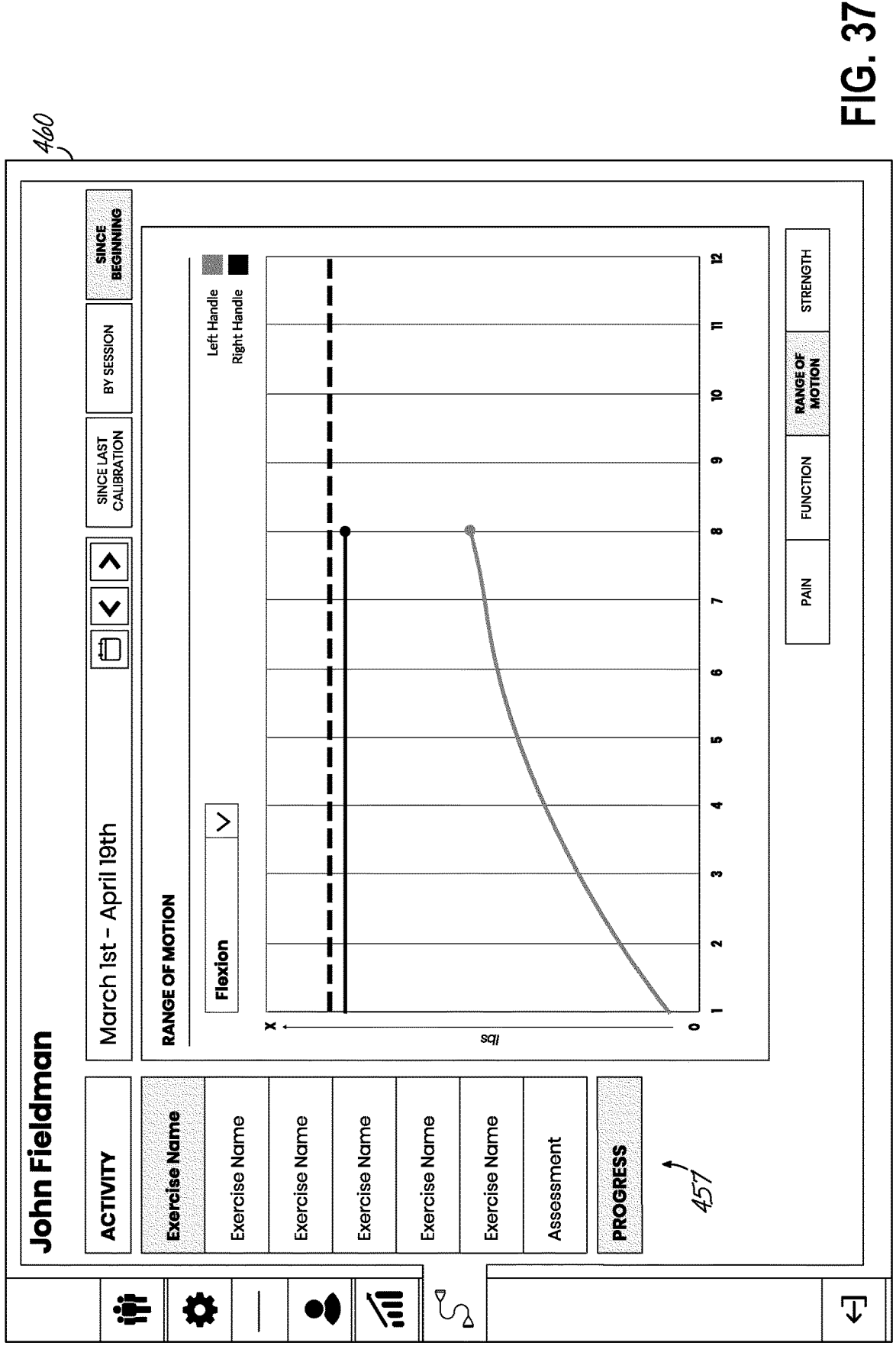

FIGS. 36 and 37 depict an exemplary patient goal setting screen 458, and an exemplary patient goal tracking screen 460. During a first clinic visit, the physical therapist and patient may mutually determine what goals they would like to focus on based off desired and expected outcomes post-rehabilitation. The patient may have the option to select one or more criteria to define their goals. These criteria may include pain, function, strength, or range of motion. Physical therapists may then review progress towards goals during in-clinic visits. In addition, patients may receive custom feedback and reminders before, during, or after their at-home sessions based off which goals they initially select.

Advantageously, the therapist application may facilitate remote treatment of patients by supporting virtual visits between the patient and therapist, or a doctor who has access to data from the therapist application. The graphical views provided by the therapist application show the patient's progress with respect to treatment criteria, such as pace, range of motion, form, and exertion, in a manner analogous to witnessing actual performance of the prescribed exercises. This may enable therapists or doctors to accurately determine patient progress and design new exercise sessions or modify existing treatment plans in accordance therewith without the patient having to be physically present. New or modified exercise sessions and treatment plans can then be stored in the database and downloaded into the patient device 16 without the patient having to physically visit the therapist or doctor.

Figure 38:
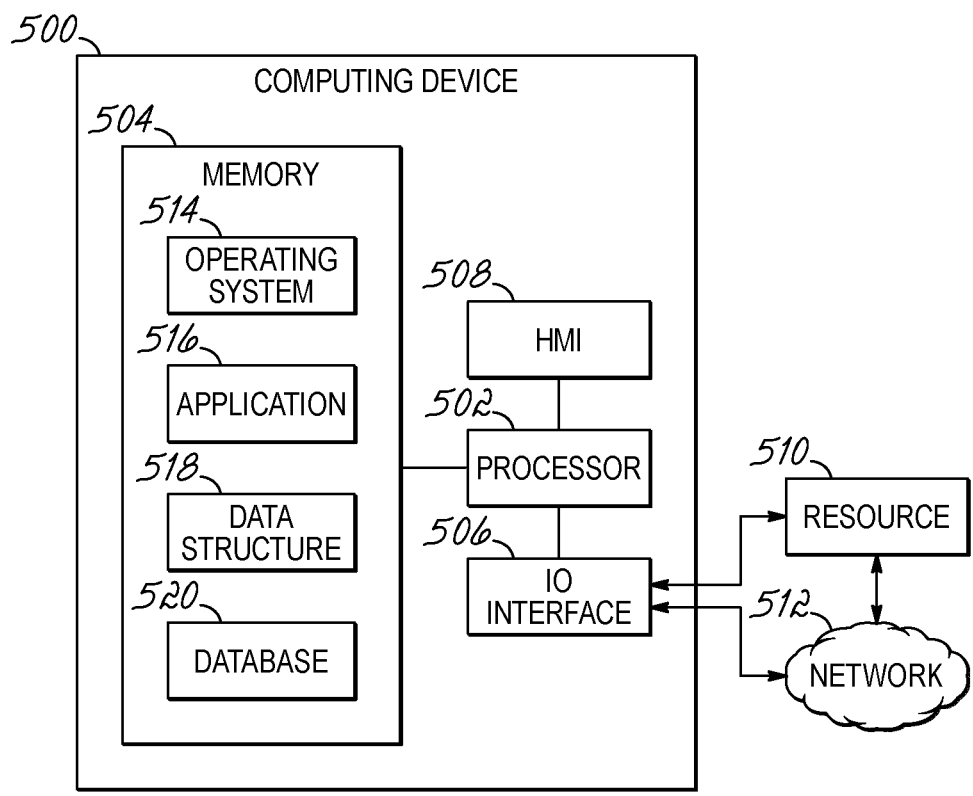
FIG. 38 is a diagrammatic view of a computer that may be used to implement one or more of the components or processes shown in FIGS. 1-37.

Referring now to FIG. 38, embodiments of the present invention described above, or portions thereof, may be implemented using one or more computing devices or systems, such as exemplary computer 500. The computer 500 may include a processor 502, a memory 504, an input/output (I/O) interface 506, and a Human Machine Interface (HMI) 508. The computer 500 may also be operatively coupled to one or more external resources 510 via the network 512 or I/O interface 506. External resources may include, but are not limited to, servers, databases, mass storage devices, peripheral devices, cloud-based network services, or any other resource that may be used by the computer 500.

The processor 502 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions stored in memory 504. Memory 504 may include a single memory device or a plurality of memory devices including, but not limited to, read-only memory (ROM), random access memory (RAM), volatile memory, non-volatile memory, static random access memory (SRAM), dynamic random access memory (DRAM), flash memory, cache memory, or data storage devices such as a hard drive, optical drive, tape drive, volatile or non-volatile solid state device, or any other device capable of storing data.

The processor 502 may operate under the control of an operating system 514 that resides in memory 504. The operating system 514 may manage computer resources so that computer program code embodied as one or more computer software applications, such as an application 516 residing in memory 504, may have instructions executed by the processor 502. In an alternative embodiment, the processor 502 may execute the application 516 directly, in which case the operating system 514 may be omitted. One or more data structures 518 may also reside in memory 504, and may be used by the processor 502, operating system 514, or application 516 to store or manipulate data.

The I/O interface 506 may provide a machine interface that operatively couples the processor 502 to other devices and systems, such as the external resource 510 or the network 512. The application 516 may thereby work cooperatively with the external resource 510 or network 512 by communicating via the I/O interface 506 to provide the various features, functions, applications, processes, or modules comprising embodiments of the present invention. The application 516 may also have program code that is executed by one or more external resources 510, or otherwise rely on functions or signals provided by other system or network components external to the computer 500. Indeed, given the nearly endless hardware and software configurations possible, persons having ordinary skill in the art will understand that embodiments of the present invention may include applications that are located externally to the computer 500, distributed among multiple computers or other external resources 510, or provided by computing resources (hardware and software) that are provided as a service over the network 512, such as a cloud computing service.

The HMI 508 may be operatively coupled to the processor 502 of computer 500 to allow a patient to interact directly with the computer 500. The HMI 508 may include video or alphanumeric displays, a touch screen, a speaker, and any other suitable audio and visual indicators capable of providing data to the patient. The HMI 508 may also include input devices and controls such as an alphanumeric keyboard, a pointing device, keypads, pushbuttons, control knobs, microphones, etc., capable of accepting commands or input from the patient and transmitting the entered input to the processor 502.

A database 520 may reside in memory 504, and may be used to collect and organize data used by the various systems and modules described herein. The database 520 may include data and supporting data structures that store and organize the data. In particular, the database 520 may be arranged with any database organization or structure including, but not limited to, a relational database, a hierarchical database, a network database, or combinations thereof. A database management system in the form of a computer software application executing as instructions on the processor 502 may be used to access the information or data stored in records of the database 520 in response to a query, which may be dynamically determined and executed by the operating system 514, other applications 516, or one or more modules.

In general, the routines executed to implement the embodiments of the present invention, whether implemented as part of an operating system or a specific application, component, program, object, module or sequence of instructions, or a subset thereof, may be referred to herein as "computer program code," or simply "program code." Program code typically comprises computer-readable instructions that are resident at various times in various memory and storage devices in a computer and that, when read and executed by one or more processors in a computer, cause that computer to perform the operations necessary to execute operations or elements embodying the various aspects of the embodiments of the present invention. Computer-readable program instructions for carrying out operations of the embodiments of the present invention may be, for example, assembly language, source code, or object code written in any combination of one or more programming languages.

Various program code described herein may be identified based upon the application within which it is implemented in specific embodiments of the present invention. However, it should be appreciated that any particular program nomenclature which follows is used merely for convenience, and thus the present invention should not be limited to use solely in any specific application identified or implied by such nomenclature. Furthermore, given the generally endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the embodiments of the present invention are not limited to the specific organization and allocation of program functionality described herein.

The program code embodied in any of the applications/modules described herein is capable of being individually or collectively distributed as a computer program product in a variety of different forms. In particular, the program code may be distributed using a computer-readable storage medium having computer-readable program instructions thereon for causing a processor to carry out aspects of the embodiments of the present invention.

Computer-readable storage media, which is inherently non-transitory, may include volatile and non-volatile, and removable and non-removable tangible media implemented in any method or technology for storage of data, such as computer-readable instructions, data structures, program modules, or other data. Computer-readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store data and which can be read by a computer. A computer-readable storage medium should not be construed as transitory signals per se (e.g., radio waves or other propagating electromagnetic waves, electromagnetic waves propagating through a transmission media such as a waveguide, or electrical signals transmitted through a wire). Computer-readable program instructions may be downloaded to a computer, another type of programmable data processing apparatus, or another device from a computer-readable storage medium or to an external computer or external storage device via a network.

Computer-readable program instructions stored in a computer-readable medium may be used to direct a computer, other types of programmable data processing apparatuses, or other devices to function in a particular manner, such that the instructions stored in the computer-readable medium produce an article of manufacture including instructions that implement the functions, acts, or operations specified in the flowcharts, sequence diagrams, or block diagrams. The computer program instructions may be provided to one or more processors of a general purpose computer, a special purpose computer, or other programmable data processing apparatus to produce a machine, such that the instructions, which execute via the one or more processors, cause a series of computations to be performed to implement the functions, acts, or operations specified in the text of the specification, flowcharts, sequence diagrams, or block diagrams.

The flowcharts and block diagrams depicted in the figures illustrate the architecture, functionality, or operation of possible implementations of systems, methods, or computer program products according to various embodiments of the present invention. In this regard, each block in the flowchart or block diagrams may represent a module, segment, or portion of instructions, which comprises one or more executable instructions for implementing the specified logical function or functions.

In certain alternative embodiments, the functions, acts, or operations specified in the flowcharts, sequence diagrams, or block diagrams may be re-ordered, processed serially, or processed concurrently consistent with embodiments of the present invention. Moreover, any of the flowcharts, sequence diagrams, or block diagrams may include more or fewer blocks than those illustrated consistent with embodiments of the present invention. It should also be understood that each block of the block diagrams or flowcharts, or any combination of blocks in the block diagrams or flowcharts, may be implemented by a special purpose hardware-based system configured to perform the specified functions or acts, or carried out by a combination of special purpose hardware and computer instructions.

The terminology used herein is for the purpose of describing particular embodiments only and is not intended to be limiting of the embodiments of the present invention. As used herein, the singular forms "a", "an" and "the" are intended to include both the singular and plural forms, and the terms "and" and "or" are each intended to include both alternative and conjunctive combinations, unless the context clearly indicates otherwise. It will be further understood that the terms "comprises" or "comprising," when used in this specification, specify the presence of stated features, integers, actions, steps, operations, elements, or components, but do not preclude the presence or addition of one or more other features, integers, actions, steps, operations, elements, components, or groups thereof. Furthermore, to the extent that the terms "includes", "having", "has", "with", "comprised of", or variants thereof are used in either the detailed description or the claims, such terms are intended to be inclusive in a manner similar to the term "comprising".

While all the present invention has been illustrated by a description of various embodiments, and while these embodiments have been described in considerable detail, it is not the intention of the Applicant to restrict or in any way limit the scope of the appended claims to such detail. Additional advantages and modifications will readily appear to those skilled in the art. The present invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. An apparatus, comprising:
   a human-device interface;
   a motion sensor coupled to, and supported by, the human-device interface;
   a controller configured to receive first motion data from the motion sensor and transmit the first motion data to a first computing device,
   the first computing device displaying a first graphical element that depicts a first movement of the human-device interface based on the first motion data;
   a network database, wherein the controller is configured to transmit the first motion data to the network database; and a second computing device configured to retrieve the first motion data from the network database and display a second graphical element that depicts the first movement of the human-device interface based on the first motion data, wherein the first graphical element depicts an animated figure performing the exercise, and a movement of the animated figure is based on a target motion, a current motion, or both the target motion and the current motion.

2. The apparatus of claim 1, further comprising:
a source of resistance.

3. The apparatus of claim 2, further comprising:
a force sensor configured to detect an amount of force being generated by the source of resistance.

4. The apparatus of claim 1, wherein the human-device interface comprises a grip including one or more transducers.

5. The apparatus of claim 4, wherein the one or more transducers includes at least one of a pressure sensor and a haptic device.

6. The apparatus of claim 1, wherein the first computing device is a patient device, and the second computing device is a therapist device.

7. The apparatus of claim 1, wherein the first computing device is configured to:
determine the target motion based on the first motion data;
receive second motion data indicative of a second movement;
determine the current motion based on the second motion data;
compare the current motion to the target motion;
in response to the current motion matching the target motion, display a second graphical element indicating an exercise is being performed properly; and
in response to the current motion not matching the target motion, providing feedback indicating the exercise is not being performed properly.

8. The apparatus of claim 7, wherein the first computing device is configured to determine the target motion by:
receiving a first signal from the second computing device;
in response to receiving the first signal, begin recording the first motion data; and
in response to receiving a second signal from the second computing device, saving the recorded data.

9. The apparatus of claim 7, wherein the first computing device is further configured to:
in response to the current motion not matching the target motion, cause at least a portion of the animated figure to provide feedback indicating that the exercise is being performed improperly; and
display a third graphical element that provides feedback indicating how to correct the current motion to match the target motion.

10. The apparatus of claim 7, wherein the human-device interface comprises a grip including a haptic device, and the first computing device is further configured to:
in response to the current motion not matching the target motion, cause the haptic device to provide feedback indicating that the exercise is being performed improperly.

11. The apparatus of claim 7, wherein the first computing device is further configured to:
in response to the current motion not matching the target motion, emit an auditory warning.

12. A method, comprising:
receiving, at a first computing device, first motion data from a motion sensor coupled to, and supported by, a human-device interface, the first motion data indicative of a first movement;
displaying, on the first computing device, a first graphical element that depicts the first movement of the human-device interface based on the first motion data;
transmitting the first motion data to a network database;
retrieving, at a second computing device, the first motion data from the network database; and
displaying, on the second computing device, a second graphical element that depicts the first movement of the human-device interface based on the first motion data,
wherein the first graphical element depicts an animated figure performing the exercise, and a movement of the animated figure is based on a target motion, a current motion, or both the target motion and the current motion.

13. The method of claim 12, further comprising:
determining the target motion based on the first motion data;
receiving second motion data from the motion sensor indicative of a second movement;
determining the current motion based on the second motion data;
comparing the current motion to the target motion;
in response to the current motion matching the target motion, displaying a second graphical element indicating an exercise is being performed properly; and
in response to the current motion not matching the target motion, providing feedback indicating the exercise is not being performed properly.

14. The method of claim 13, wherein determining the target motion based on the first motion data comprises:
receiving a first signal from the second computing device;
in response to receiving the first signal, begin recording the first motion data; and
in response to receiving a second signal from the second computing device, saving the recorded data.

15. A computer program product comprising:
a non-transitory computer-readable storage medium; and
program code stored on the non-transitory computer-readable storage medium that, when executed by one or more processors, causes the one or more processors to perform the method of claim 12.

16. An apparatus, comprising:
a human-device interface;
a motion sensor operatively coupled to the human-device interface; and
a controller configured to receive first motion data from the motion sensor and transmit the first motion data to a first computing device,
the first computing device displaying a first graphical element that depicts a first movement of the human-device interface based on the first motion data,
wherein the first computing device is configured to determine a target motion by:
receiving a first signal from a second computing device;
in response to receiving the first signal, begin recording the first motion data; and
in response to receiving a second signal from the second computing device, saving the recorded data.

17. The apparatus of claim 16, wherein the first computing device is a patient device, and the second computing device is a therapist device.

18. The apparatus of claim 16, wherein the first computing device is configured to:
- determine the target motion based on the first motion data;
- receive second motion data indicative of a second movement;
- determine the current motion based on the second motion data;
- compare the current motion to the target motion;
- in response to the current motion matching the target motion, display a second graphical element indicating an exercise is being performed properly; and
- in response to the current motion not matching the target motion, providing feedback indicating the exercise is not being performed properly.

19. The apparatus of claim 18, wherein the first computing device is further configured to:
- in response to the current motion not matching the target motion, cause at least a portion of the animated figure to provide feedback indicating that the exercise is being performed improperly; and
- display a third graphical element that provides feedback indicating how to correct the current motion to match the target motion.

20. The apparatus of claim 18, wherein the human-device interface comprises a grip including a haptic device, and the first computing device is further configured to:
- in response to the current motion not matching the target motion, cause the haptic device to provide feedback indicating that the exercise is being performed improperly.

21. The apparatus of claim 18, wherein the first computing device is further configured to:
- in response to the current motion not matching the target motion, emit an auditory warning.

* * * * *